United States Patent
Burkinshaw et al.

(10) Patent No.: US 9,408,711 B2
(45) Date of Patent: Aug. 9, 2016

(54) UNITARY SPINAL DISC IMPLANT

(71) Applicants: Brian D. Burkinshaw, Pflugerville, TX (US); Jonathan Stupka, Lakeway, TX (US)

(72) Inventors: Brian D. Burkinshaw, Pflugerville, TX (US); Jonathan Stupka, Lakeway, TX (US)

( * ) Notice: Subject to any disclaimer, the term of this patent is extended or adjusted under 35 U.S.C. 154(b) by 0 days.

(21) Appl. No.: 14/177,109

(22) Filed: Mar. 2, 2014

(65) Prior Publication Data

US 2015/0245916 A1    Sep. 3, 2015

(51) Int. Cl.
*A61F 2/44* (2006.01)
*A61F 2/30* (2006.01)

(52) U.S. Cl.
CPC ............... *A61F 2/442* (2013.01); *A61F 2/4455* (2013.01); *A61F 2/4465* (2013.01); *A61F 2002/3021* (2013.01); *A61F 2002/3093* (2013.01); *A61F 2002/30205* (2013.01); *A61F 2002/30217* (2013.01); *A61F 2002/30224* (2013.01); *A61F 2002/30227* (2013.01); *A61F 2002/30235* (2013.01); *A61F 2002/30448* (2013.01); *A61F 2002/30563* (2013.01); *A61F 2002/30604* (2013.01); *A61F 2002/30616* (2013.01); *A61F 2002/30769* (2013.01); *A61F 2002/30772* (2013.01); *A61F 2002/30795* (2013.01); *A61F 2002/30841* (2013.01);
(Continued)

(58) Field of Classification Search
CPC ....................... A61F 2/44–2/447; A61F 2/4611
See application file for complete search history.

(56) References Cited

U.S. PATENT DOCUMENTS

| 4,349,921 A | 9/1982 | Kuntz |
| 4,863,477 A | 9/1989 | Monson |
| 4,932,969 A | 6/1990 | Frey et al. |

(Continued)

OTHER PUBLICATIONS

PCT/US2014/15850 International Search Report and Written Opinion dated Sep. 25, 2014.
(Continued)

*Primary Examiner* — Jan Christopher Merene
*Assistant Examiner* — Steven Cotroneo
(74) *Attorney, Agent, or Firm* — Brian Burkinshaw

(57) ABSTRACT

A unitary intervertebral device, having no moving components is provided for non-fusion articulation applications. The interbody articulating device allows for limited flexion and rotation between adjacent vertebrae, helping to preserve or restore near-normal motion between adjacent vertebrae. Rotational motion is achieved through one or more protrusions incorporated into the spinal interbody device. In one articulating form, a first protrusion extends perpendicularly from the superior aspect of the disc-shaped interbody device to form a spike or rotational protrusion, while a second protrusion extends axially from the inferior aspect of the interbody device to form a second spike or rotational protrusion. Protrusions preferably extend perpendicular from the apex of both the first and second arcuate articulating surfaces. In another form, a single protrusion extends axially from the superior aspect of a circular-shape of the interbody device to form a spike or anchoring protrusion, while the inferior surface may be slightly rounded and/or comprising a bone-ingrowth promoting surface. In another form, one or both of the first and/or second arcuate surfaces may be highly polished. Numerous planar geometries are described to define various profiles of the disc replacement implant which may be utilized, including irregular Reuleaux polygons. Numerous variations of the disc replacement and methods of use are described. Similarly configured fusion salvage devices are also described.

20 Claims, 11 Drawing Sheets

(52) U.S. Cl.
CPC ............. *A61F 2002/30906* (2013.01); *A61F 2230/0067* (2013.01); *A61F 2230/0069* (2013.01)

(56) References Cited

U.S. PATENT DOCUMENTS

| | | | |
|---|---|---|---|
| 4,936,848 A * | 6/1990 | Bagby | A61F 2/4455 606/247 |
| 5,071,437 A | 12/1991 | Steffee | |
| 5,645,596 A * | 7/1997 | Kim | A61F 2/442 623/17.16 |
| 5,865,846 A * | 2/1999 | Bryan | A61B 17/686 128/898 |
| 5,888,226 A * | 3/1999 | Rogozinski | A61F 2/442 623/17.16 |
| 6,001,130 A | 12/1999 | Bryan et al. | |
| 6,383,221 B1 * | 5/2002 | Scarborough | A61F 2/4455 623/17.11 |
| 6,902,581 B2 * | 6/2005 | Walkenhorst | A61F 2/446 623/17.16 |
| 7,001,433 B2 * | 2/2006 | Songer | A61F 2/442 606/247 |
| 7,025,787 B2 | 4/2006 | Bryan | |
| D598,105 S | 8/2009 | Krishna | |
| 7,601,174 B2 | 10/2009 | Kelly | |
| 7,641,692 B2 | 1/2010 | Bryan et al. | |
| 7,662,185 B2 * | 2/2010 | Alfaro | A61F 2/4455 623/17.11 |
| 7,695,516 B2 | 4/2010 | Zeegers | |
| 7,901,459 B2 | 3/2011 | Hodges | |
| 7,905,922 B2 * | 3/2011 | Bergeron | A61F 2/442 623/17.11 |
| 8,038,920 B2 | 10/2011 | Denoziere | |
| 8,092,542 B2 | 1/2012 | Bryan | |
| 8,226,723 B2 | 7/2012 | Conti | |
| 8,262,731 B2 | 9/2012 | Songer et al. | |
| 8,603,171 B2 | 12/2013 | McClellan, III | |
| 8,926,703 B2 | 1/2015 | Michelson | |
| 2003/0195628 A1 * | 10/2003 | Bao | A61B 17/7097 623/17.12 |
| 2005/0149188 A1 | 7/2005 | Cook et al. | |
| 2005/0251260 A1 | 11/2005 | Gerber | |
| 2006/0085077 A1 | 4/2006 | Cook et al. | |
| 2006/0276790 A1 | 12/2006 | Dawson | |
| 2007/0118224 A1 | 5/2007 | Shah et al. | |
| 2007/0276495 A1 | 11/2007 | Aaron | |
| 2009/0018663 A1 | 1/2009 | Cook et al. | |
| 2009/0069897 A1 | 3/2009 | Butler et al. | |
| 2009/0216331 A1 | 8/2009 | Grotz | |
| 2011/0035006 A1 | 2/2011 | Cook et al. | |
| 2011/0035010 A1 | 2/2011 | Harrington | |
| 2012/0191193 A1 * | 7/2012 | Trieu | A61F 2/4611 623/17.16 |

OTHER PUBLICATIONS

PCT/US2014/15850 International Preliminary Report on Patentability dated Aug. 20, 2015.

* cited by examiner

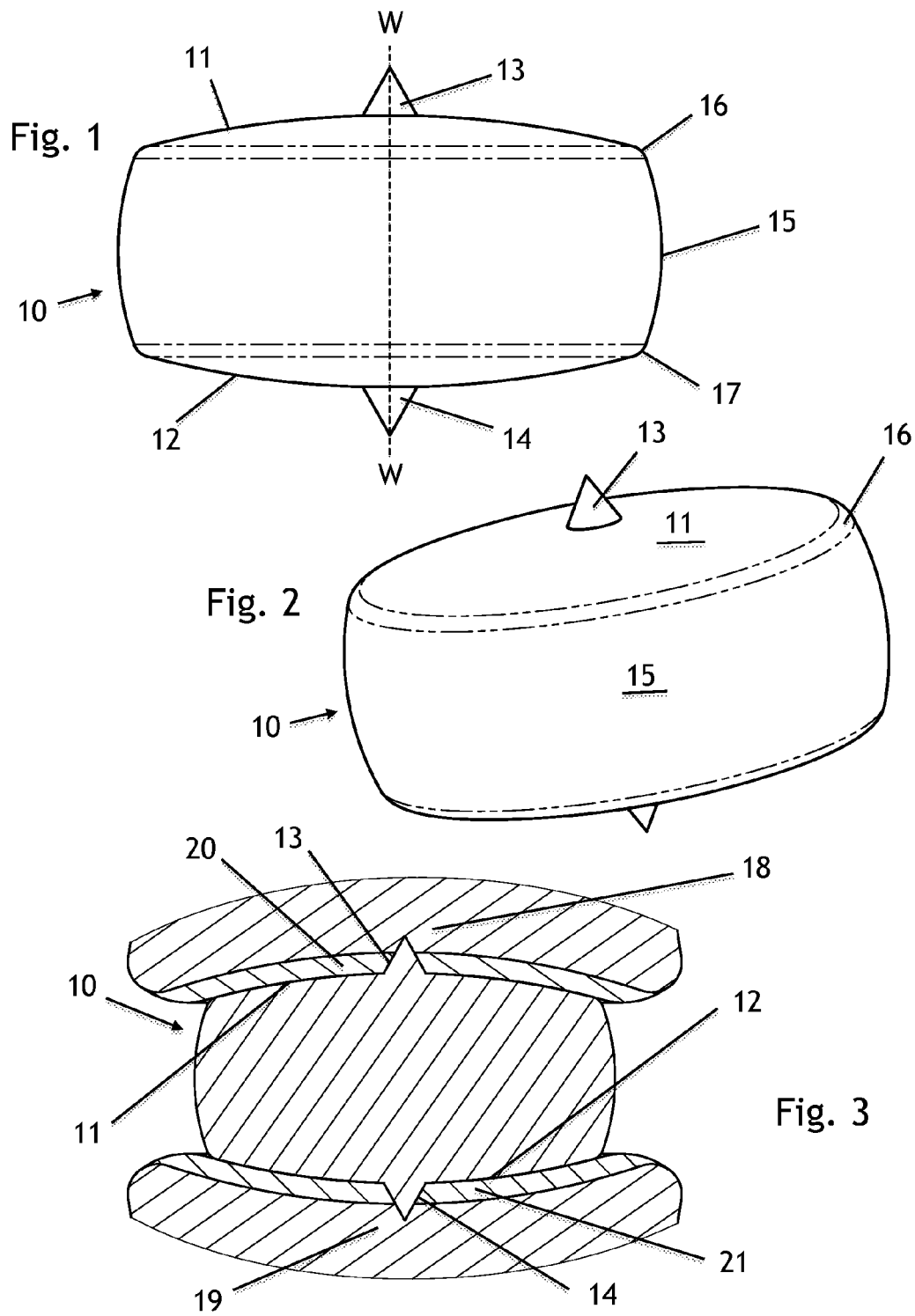

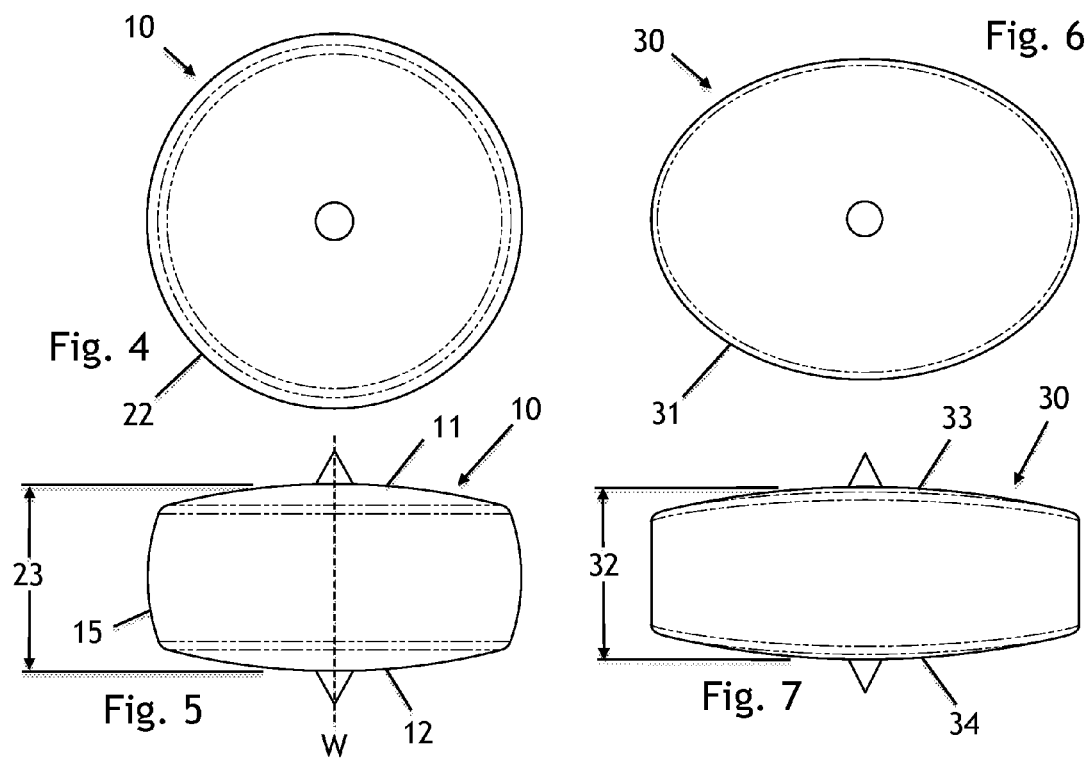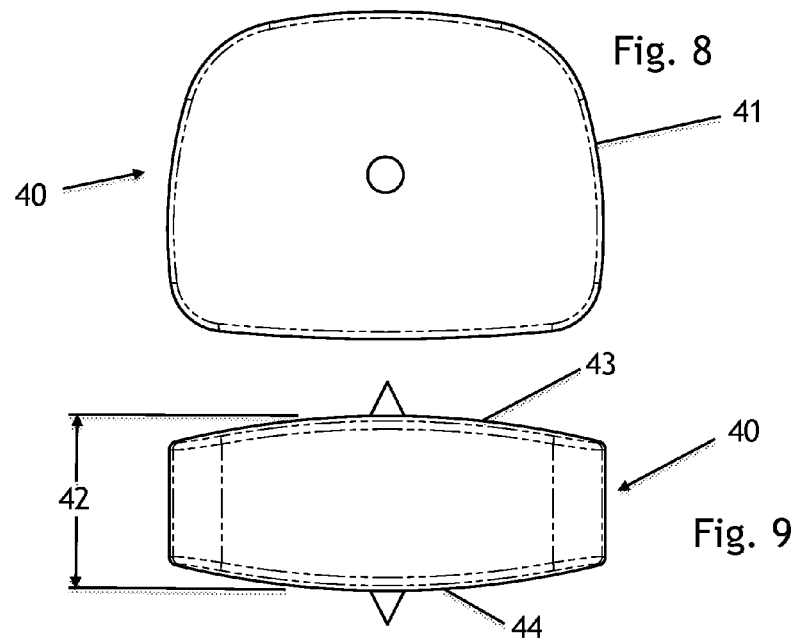

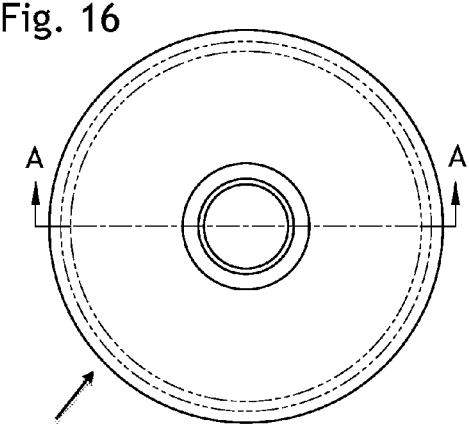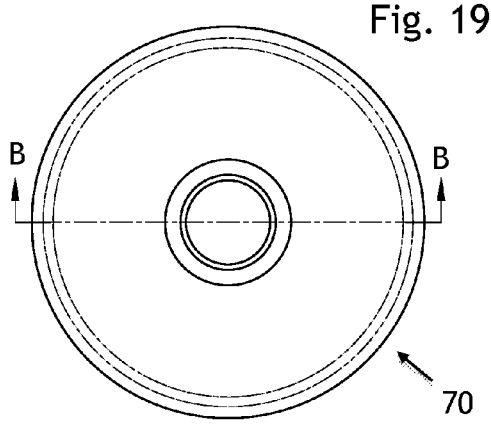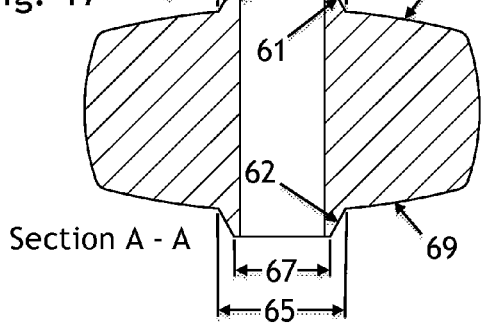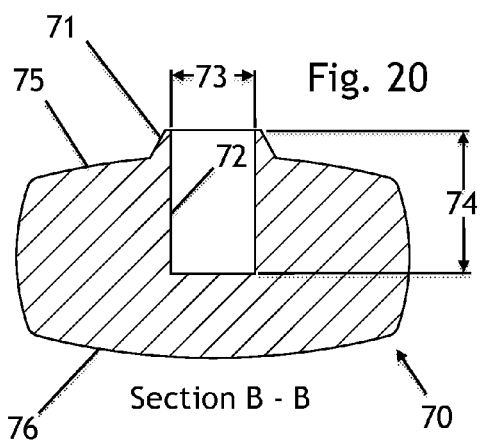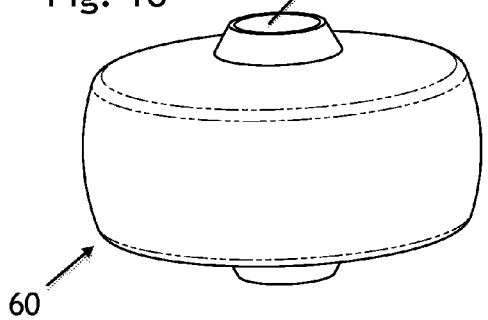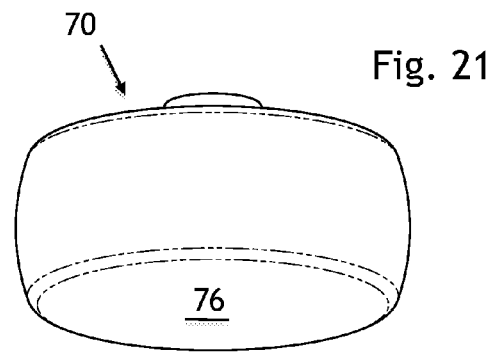

Section C - C

Section D - D

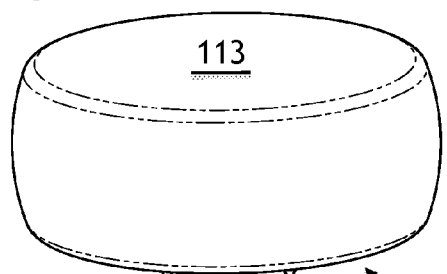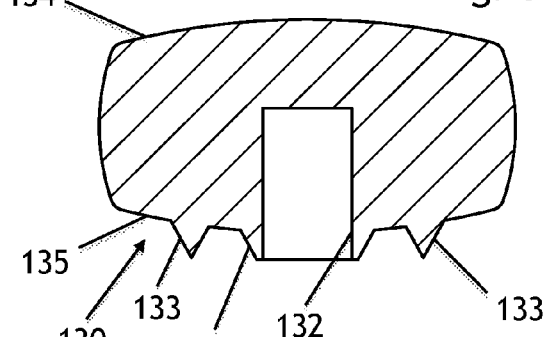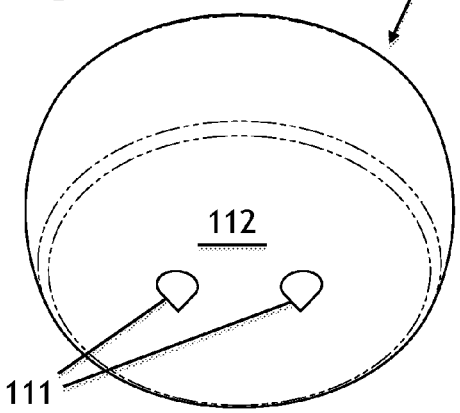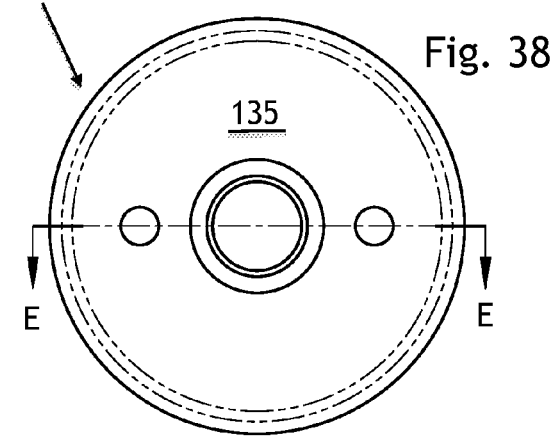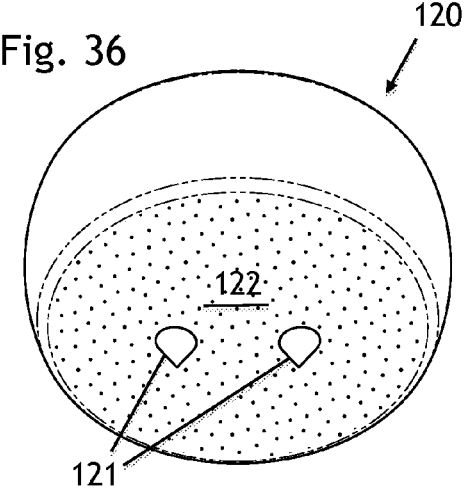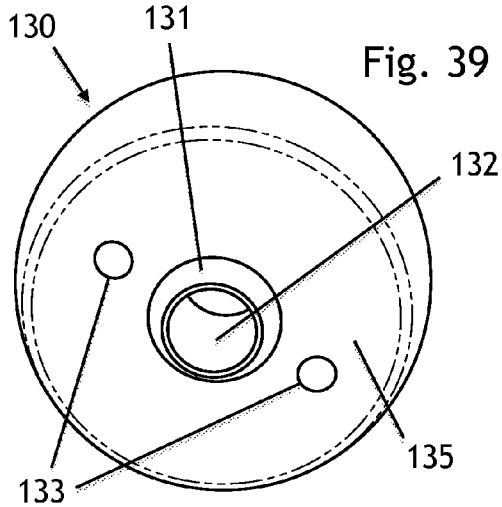

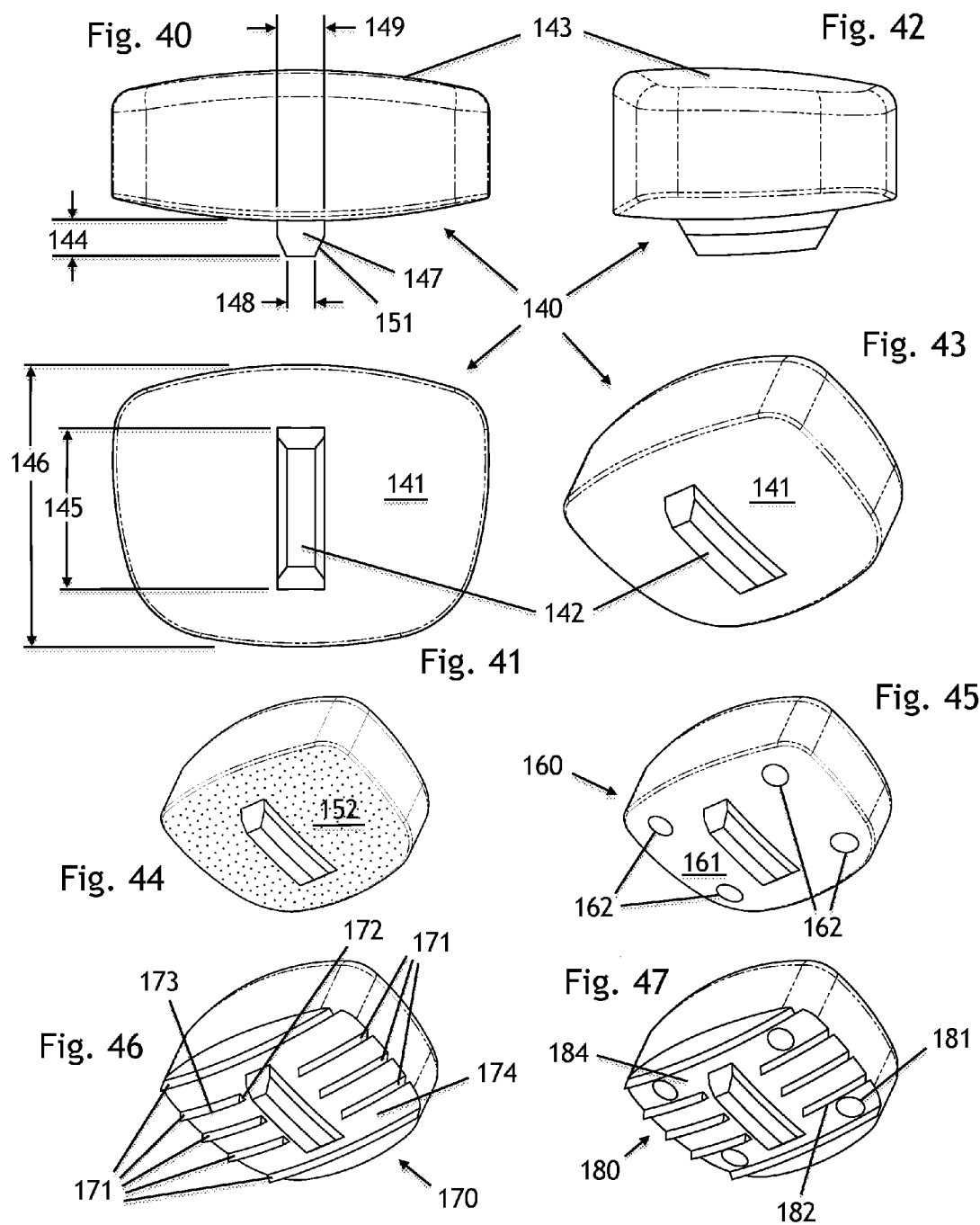

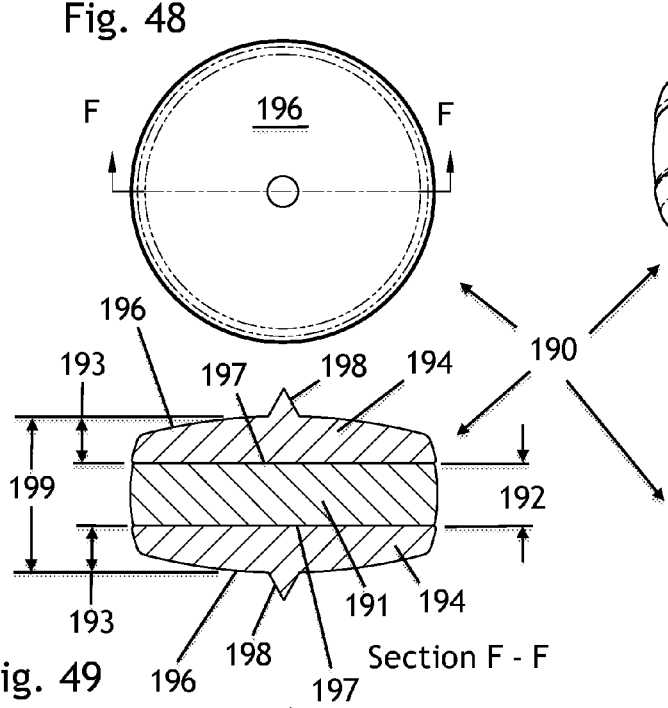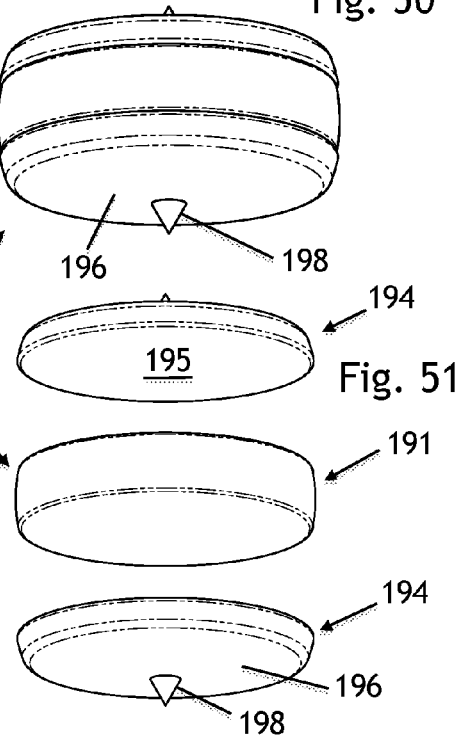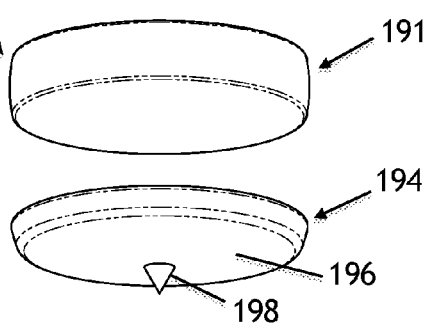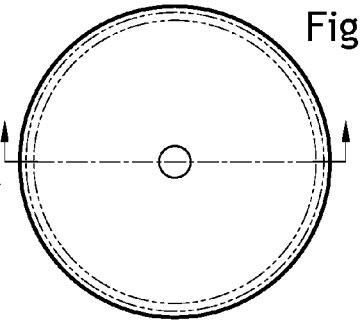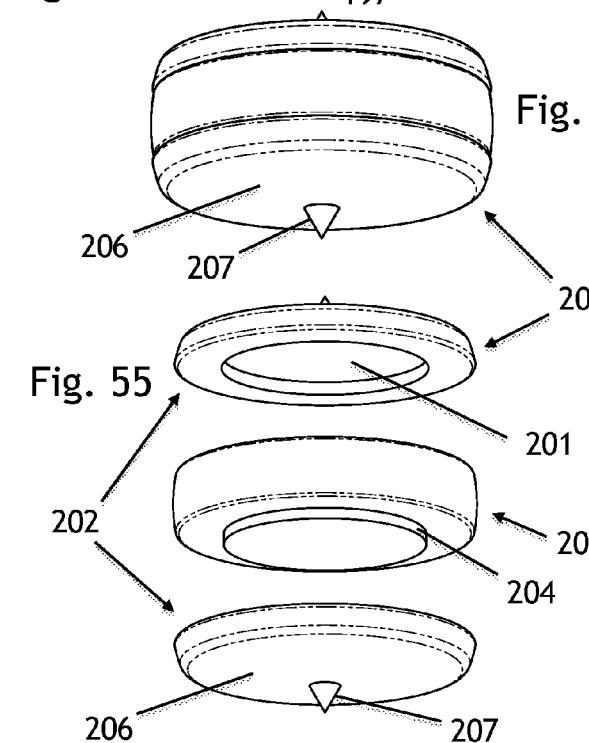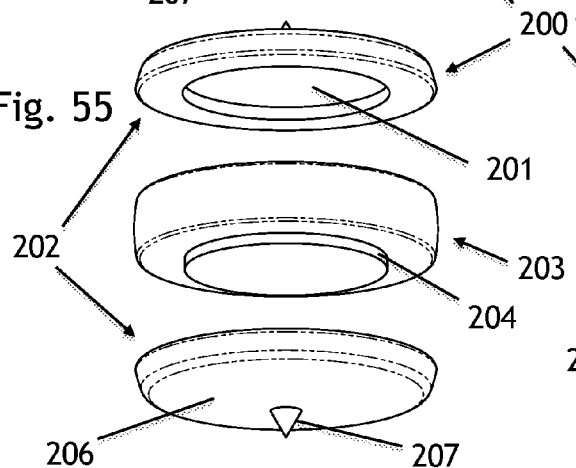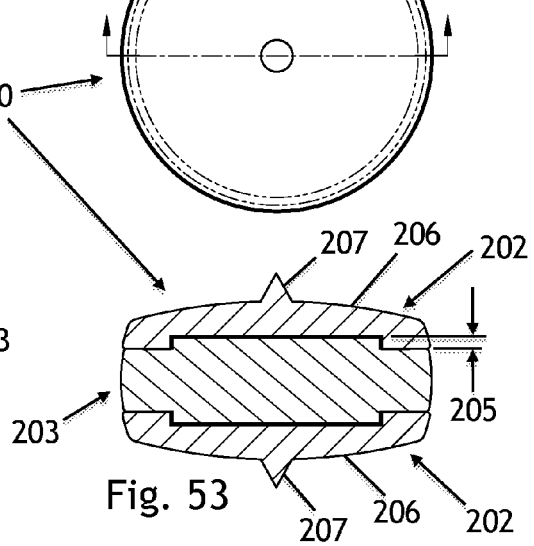

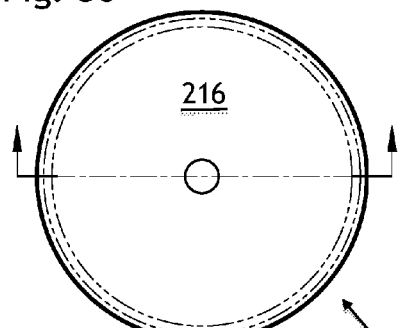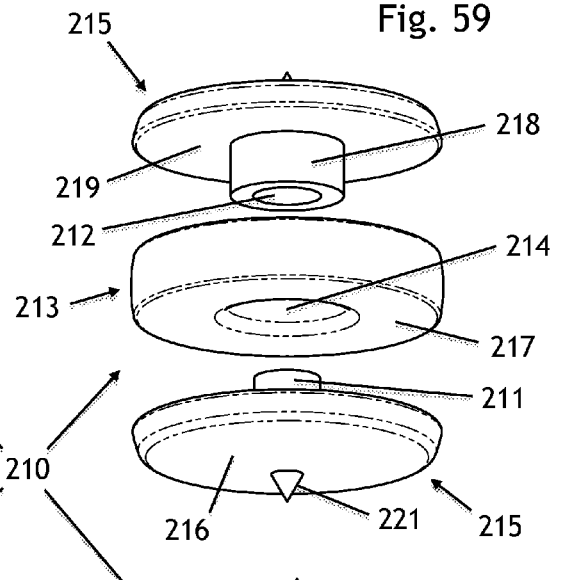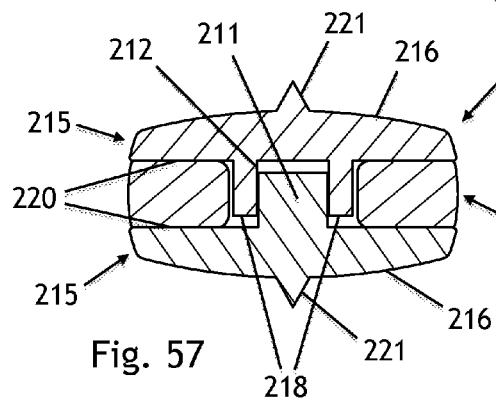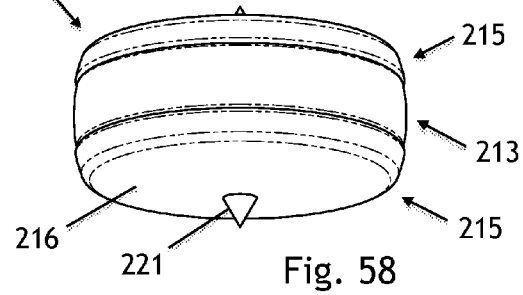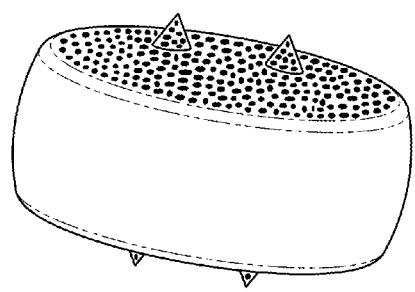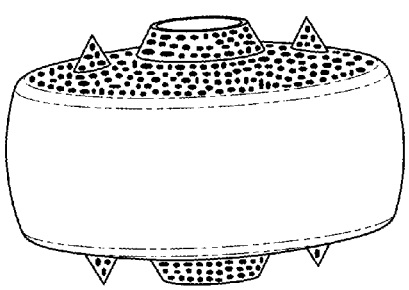

UNITARY SPINAL DISC IMPLANT

CROSS-REFERENCE

This application claims the benefit of U.S. Provisional Application No. 61/786,193, filed Mar. 14, 2013, which applications are incorporated herein by reference.

BACKGROUND OF THE INVENTION

Artificial disc technology has been employed as a surgical approach to repair or replace damaged spinal discs in an attempt to relieve debilitating neck and back pain, and to maintain or restore intervertebral spacing while attempting to minimize their constraining effects on the normal biomechanical movement of the spine. The quest for a more physiologic device to accomplish these goals began in the 1950s and continues to this day.

Total disc replacement is still a relatively new, promising field of spine implant technology that has the potential to revolutionize the treatment of degenerative disc disease. It is clear from both short-term in-vitro and clinical data, that disc replacements can successfully preserve the motion of a treated spine and significantly reduce the potential incidence of adjacent level disc degeneration. But unfortunately, not unlike as many as 40% of spinal fusions performed worldwide, disc replacements may also need to be revised due to poor implantation technique, component wear, or failure of the device, to name but a few.

Clinical data has illustrated that many failures occur as a result of over-aggressive bone bed preparation or excessive protuberances on the implants both of which can result in compromise of the vertebral endplates. Other data suggests that many design failures resulted from point loading or inadequate load distribution across the endplate. Still other designs suffer from poor choices of materials for articular wear bearings, oxidation, and/or inadequate long-term wear characteristics between device sub-components. Each of the aforementioned deficiencies may ultimately result in subsidence, loss of designed function, or even spontaneous fusion.

It may be a generation before sufficient data emerges to clearly delineate the long-term successful designs from the catastrophic failures, but given that most of the currently pending or recently approved artificial disc implants in the market are based on design fundamentals utilized in other orthopedic applications that have already been demonstrated to fail for predictable reasons, one might expect to see many of these designs fail in similar fashion for the same reasons. Accordingly, there remains a need for better artificial disc technology that addresses these shortcomings by providing an artificial disc that does not significantly inhibit spinal movement, minimizes any potential for wear between disc components and or vertebral bodies, improves upon the surgical technique utilized to implant them, reduces the potential for histocytic foreign body and/or inflammatory response, and provides physiologic load bearing and joint spacing functions akin to the normal, healthy spinal disc. In addition, there also remains a need for better salvage and fusion devices to replace other failed artificial discs.

SUMMARY OF THE INVENTION

A unitary intervertebral device, having no independent moving components is provided for non-fusion articulation applications. The interbody articulating device allows for limited flexion and rotation between adjacent vertebrae, helping to preserve or restore near-normal motion between adjacent vertebrae. Rotational motion is achieved around one or more protrusions incorporated into the spinal interbody device.

In one aspect the invention is an implant comprising a unitary structure, having no independent articulating components, containing integrated features to replace the articulating function of the natural spinal disc, and allowing a spinal joint into which it has been implanted, to closely approximate the flexion biomechanics and rotational motion of a reasonably healthy joint.

It is another object of this invention to provide a highly polished, high wettability surface finish to the arcuate surface(s) of a discus-shaped implant which makes broad contact with the endplates of the vertebral bodies in order to improve rotational motion with reduced friction and wear.

It is another object of this invention to significantly reduce or eliminate $3^{rd}$ body wear particles resulting from rolling or sliding friction between the articulating surfaces of an artificial disc and the vertebral endplates and/or endplate cartilage of the spine.

It is another object of this invention to significantly reduce or eliminate any $3^{rd}$ body wear particles resulting from micromotion or sliding friction between assembled sub-components of the artificial disc such as between a poly bearing surface and an endplate to which it may be captured, fixed or otherwise assembled.

It is another object of this invention to maximize the surface area coverage of the vertebral endplate with the implant, to minimize the potential for implant subsidence, spontaneous fusion, and localized compression stresses.

It is yet another object of at least one variation of this invention to preserve as much native endplate cartilage as possible to promote and improve articulation between the vertebra and the implant, rather than intentionally removing native cartilage and abrading endplate surfaces to induce bone ingrowth and fusion to the implant on one or both adjacent endplate surfaces, as is done with other spinal disc replacements.

In one articulating form, a first protrusion extends perpendicularly from the superior (first) aspect of a discus-shape of the interbody device to form a spike or rotational protrusion, while a second protrusion extends axially from the inferior (second) aspect of the interbody device to form a second spike or rotational protrusion. Protrusions preferably extend perpendicularly from the apex of both the first and second arcuate articulating surfaces about the central axis.

In another form, a single protrusion extends axially from the superior aspect of the interbody device to form a spike, pivot point, or anchoring protrusion, while the inferior surface is a slightly rounded articulating bearing surface. One or both of the first and/or second arcuate surfaces may be highly polished.

In yet other variations, the implant is configured to provide a polished articulating surface on one bearing surface and a fusion surface on the opposite bearing surface.

In other articulating and non-articulating forms, tether features are described for providing ingrowth through the endplate to an adjacent vertebral body.

In still other configurations, variations of a unitary device are described comprising an intermediate core that is permanently affixed between the outer articulating bearing surfaces, to act as an alternative cushioning apparatus, providing a dampening feature for the spine in place of the defective natural spinal disc. Both articulating and fusion versions of the device are described.

Numerous geometries are described to define functional profiles of the disc replacement implant which may be utilized, including regular and irregular Reuleaux polygons. Numerous variations of the disc replacement and methods of use are described.

Also described herein are similarly configured fusion salvage devices comprising protrusions, tether features, ingrowth features and surface geometries.

Provided herein is a unitary implant adapted for placement between adjacent surfaces of a joint comprising: a first bearing surface and a second bearing surface, wherein the first and second bearing surfaces are generally convex and configured to have generally spherical bearing surface curvature that generally conforms to the concave geometry of the adjacent joint surfaces; an outer radial edge surface; a first protrusion on the first bearing surface, wherein the first protrusion is configured to contact a central portion of a first adjacent joint surface, and wherein the first protrusion is adapted to allow rotation about an axis.

In some embodiments, the unitary implant further comprises a second protrusion on the second bearing surface, wherein the second protrusion is configured to contact a central portion of a second adjacent surface, and wherein the second protrusion is adapted to allow rotation about the common axis of the first and second protrusion.

In some embodiments of the unitary implant, the first protrusion is conical. In some embodiments, the second protrusion is conical. In still other embodiments the first protrusion or second protrusion may comprise a cone, a curved cone (sometimes referred to as parabolic or hyperbolic cones), a truncated cone, or a cylinder. In some embodiments, the protrusions are different. Still further, the first protrusion or second protrusion may comprise a truncated cone with a hole about the central axis, or a cylinder with a hole about the central axis. Still further, the hole in the protrusion may be a blind hole or a thru-hole that penetrates through the entire implant.

In some embodiments, the implant comprises a truncated cone with a hole about the central axis, or a cylinder with a hole about the central axis, wherein the implant also comprises a tethering feature that is configured to promote ingrowth or attachment to the adjacent vertebra. In some embodiments, the attachment may be to just one adjacent endplate or vertebra: In other configurations, the attachment may be to both of the adjacent endplates or vertebrae.

In some embodiments, the first protrusion and/or the second protrusion is adapted to penetrate at least the cartilage of the first adjacent joint surface and/or the second adjacent joint surface, providing an extremely conservative surgical procedure. In other embodiments, the first protrusion or the second protrusion is adapted to penetrate the endplate of the first adjacent joint surface or the second adjacent joint surface.

In still other embodiments of the unitary implant comprising a first protrusion on the first bearing surface, the implant may further comprise at least a second and third protrusion on the second bearing surface, wherein the at least second and third protrusion are configured to contact a portion of a second adjacent surface, preferably penetrating at least a portion of the adjacent endplate, and wherein the at least second and third protrusion are adapted to prevent movement between the second bearing surface and the second adjacent surface.

In some embodiments of the unitary implant, the implant is generally circular in shape about a central axis. In other embodiments, the implant is non-circular in shape about a central axis. In certain preferred embodiments, the implant may comprises an elliptical planar shape or a common variant thereof.

Still further, in other preferred embodiments, the implant shape may resemble a Reuleaux polygon planar shape comprising three or more sides. The Reuleaux polygon shape may be in the form of an irregular Reuleaux polygon, wherein at least one side of the polygon is curved, or wherein at least one side has a different length than the remaining sides, or both.

In some embodiments, the implant comprises an anatomic-like bearing surface, wherein the curvature of the first bearing surface and the second bearing surface is generally spherical or near spherical. In other embodiments, the curvature of the first bearing surface and the second bearing surface is generally multi-radial in order to more closely match the native, damaged or surgically prepared endplate surface. In some embodiments, the first bearing surface and the second bearing surface geometries are the same. Alternatively, in other embodiments, the first bearing surface and the second bearing surface comprise different geometries.

Still further, in some embodiments the first bearing surface and the second bearing surface are mirrored, or symmetrical about a central transverse plane, whereas in other embodiments the first bearing surface and the second bearing surface are inclined to each other about a central transverse plane to better match or reconstruct the natural lordosis (or kyphosis) of the spine.

In some embodiments of the implant, only the first bearing surface and the first protrusion are polished articulating surfaces. In other embodiments, only the second bearing surface and the second protrusion are polished articulating surfaces. In still others, all of the bearing surfaces and protrusions are polished articulating surfaces.

In any one of the embodiments described herein, the first bearing surface or second bearing surface may comprise or be manufactured from at least one of the following materials: pyrolytic carbon, titanium, titanium nitride, tantalum, cobalt, chromium, polyethylene, PEEK® (Polyether ether ketone), Delrin®, alumina, zirconia, silicon carbide, silicon nitride, stainless steel, diamond, or a diamond like material. In some embodiments, the unitary implant may comprise a core fabricated from one material having one set of properties, and an outer bearing surface fabricated from another material having a different set of properties.

In some embodiments, the implant is an articulating implant, having applications in artificial limbs, robotics, or other joints and mechanisms. In some embodiments, the implant is a medical implant having applications for veterinary applications. In still other preferred embodiments, the implant is a human medical implant intended for the spine.

Provided herein is a unitary spinal disc implant adapted for placement between adjacent vertebral surfaces of a spinal joint comprising: a first bearing surface and a second bearing surface, wherein the first and second bearing surfaces are generally convex and configured to have a spherical curvature that generally conforms to the concave geometry of the adjacent spinal joint surfaces; an outer radial edge surface; a first protrusion on the first bearing surface, wherein the first protrusion is configured to contact a central portion of a first adjacent spinal joint surface, a second protrusion on the second bearing surface, wherein the second protrusion is configured to contact a central portion of a second adjacent spinal surface, wherein the first protrusion and second protrusion are adapted to allow rotation about a common axis.

Provided herein is a method of using a spinal disc implant wherein the method comprises providing a unitary disc implant adapted for placement between adjacent vertebral surfaces of a spinal joint, wherein the implant comprises: a first bearing surface and a second bearing surface, wherein the first bearing surface and second bearing surface are generally spherical; a first protrusion on the first bearing surface, wherein the first protrusion is configured to contact a central portion of a first adjacent spinal joint surface; a second protrusion on the second bearing surface, wherein the second protrusion is configured to contact a central portion of a second adjacent spinal surface; and wherein the first protrusion and second protrusion are adapted to allow rotation of the spinal disc implant about a common axis.

Provided herein is a unitary spinal disc implant adapted for placement between adjacent vertebral endplates comprising: a first bearing surface and an second bearing surface, wherein the first and second bearing surfaces are configured to have a geometry that conforms to the concave geometry of adjacent endplate surfaces; at least one conic protrusion on at least one bearing surface for penetrating at least one of the adjacent endplates, wherein the at least one protrusion is configured to contact a central portion of at least one adjacent vertebral endplate.

In some embodiments, the first bearing surface is an articulating surface. In some embodiments, the second bearing surface is an articulating surface. In some embodiments, the first bearing surface and second bearing surface geometries are the same. In some embodiments, the first bearing surface and second bearing surface comprise different geometries.

In some embodiments, the geometry of the first bearing surface and/or second bearing surface may be generally spherical. Alternately, the first bearing surface geometry may be generally flat to spherical.

In still other embodiments, the second bearing surface geometry is generally flat in the center, transitioning to spherical at the radial edges. Alternately the second bearing surface geometry may be generally flat with radiused edges. Still further the second bearing surface geometry may be generally flat and transitioning to a proportionately large spherical radius to replicate a worn or surgically prepared endplate surface. In even further embodiments, the first bearing surface and second bearing surface comprise slightly increasing arcuate radii of curvature from the outer [radial] edge surface to the central axis. In some embodiments, the arcuate radii of curvature of the first and second bearing surfaces are essentially mirror imaged about a central transverse plane.

In some embodiments, the first bearing surface and second bearing surface are centered about a central axis. Further still, the at least one conic protrusion is centered about the central axis. In other embodiments, the at least one conic protrusion is located off-center from the central axis.

In at least one embodiment, the first bearing surface and second bearing surface are inclined to each other about a central transverse plane, in order to provide the ability to restore the natural spinal lordotic or kyphotic curvature, wherein the anterior height of the implant may be greater than the posterior height (for restoring lordosis) or the posterior height of the implant may be greater than the anterior height (for restoring kyphosis).

In any one of the preceding embodiments, the implant is circular in shape about the central axis. Alternately, the implant is configured to be elliptical in shape about the central axis, wherein the M/L dimension is greater than the A/P dimension. Even further, the implant may be polygon in shape about the central axis, wherein the polygon comprises at least four side edges. Additionally, the polygon may have either straight or curved sides, (alternately called a Reuleaux polygon), and may also have sides with different lengths and smoothly blended intersections.

Still further, in some embodiments, the implant comprises an anterior-posterior (front to back) dimension that is greater than the overall arcuate height of the implant. This dimensional configuration can be provided in a range and may be represented by a ratio wherein the anterior-posterior dimension to the overall arcuate height is at least 1.01:1; is at least 1.1:1; is at least 1.2:1; is at least 1.5:1, or is at least 2.0:1; etc., for non-limiting example.

Further still, in some embodiments, the implant comprises a medial-lateral dimension that is greater than the overall arcuate height of the implant. This dimensional configuration can also be provided in a range and may be represented by a ratio wherein the medial-lateral dimension to the overall arcuate height is at least 1.01:1; is at least 1.1:1; is at least 1.2:1; is at least 1.5:1, or is at least 2.0:1; is at least 3.0:1; is at least 4.0:1; etc., for non-limiting example.

In some embodiments, the implant comprises at least two protrusions. In other embodiments, the implant comprises exactly two protrusions. In still other embodiments, the implant comprises at least one protrusion on at least one bearing surface, wherein the at least one protrusion is conic. Still further, in some embodiments, the at least one conic protrusion is a truncated cone comprising a base diameter with a wider girth and may further comprise an inner void. In those embodiments where the conic protrusion includes an inner void, the void may be a blind hole, or it may be a void that extends through the entire implant. In preferred embodiments the conic protrusions, and corresponding holes or voids are concentric about a central axis.

In any one of the embodiments herein, the at least one protrusion is configured to puncture the adjacent endplate when the implant is positioned between vertebrae.

In some embodiments, at least one of the first bearing surface and the second bearing surface comprises at least one fenestration. The at least one fenestration may be circular or non-circular in profile, and/or a blind void or hole. The fenestration may comprise a ridge or a groove. Alternatively, more than one fenestration may be present, with each having a different configuration.

In any one of the embodiments herein, at least one of the first bearing surface and the second bearing surface is polished, wherein the at least one polished bearing surface has a surface finish ≤4 RMS. In a preferred embodiment, the at least one of the first bearing surface and the second bearing surface is an articulating surface.

In some embodiments, exactly one of the surfaces is an articulating surface and at least a portion of the other of the surfaces is a textured surface. In some embodiments, at least a portion of at least one of the first surface and the second surface is textured.

Still further, in other embodiments, at least a portion of both the first surface and the second surface is textured. In one such preferred embodiment, both the first surface and the second surface is a non-articulating surface, wherein at least a portion of both of the first surface and the second surface is a fusion surface. In one such preferred embodiment, at least a portion of the first surface or the second surface comprises a surface finish ≥125 RMS.

In some embodiments, the implants are non-articulating salvage or fusion implants, wherein both surfaces comprise a non-articulating textured surface, and wherein the textured surface is a surface configured to receive a fixation compound. Alternatively, the textured surface is a porous surface intended to mimic cancellous bone and promote ingrowth.

Alternatively, a non-articulating surface may comprise one or more fenestrations, wherein a fenestrated surface is a surface configured to receive a fixation compound.

In some embodiments, the implant is configured for use in an articulating joint. In other embodiments the implant is configured for use in the spine of an animal. In a preferred embodiment, the implant is configured for use in the spine of a human as a spinal disc implant. In a most preferred embodiment, the implant is a unitary disc implant, having no moving components within the device.

Provided herein is an assembled disk-like implant adapted for placement between adjacent vertebral endplates comprising: a first endcap having a first outer surface and first inner surface and a first outer radial edge; an second endcap having second outer surface and second inner surface and a second outer radial edge, an intermediate core comprising an upper surface and lower surface configured to be permanently bonded between the first inner surface and the second inner surface; at least one protrusion on at least one endcap surface, wherein the at least one protrusion is configured to contact a portion of at least one adjacent vertebral endplate.

In some embodiments, the first endcap surface and second endcap surface are each configured to have an external bearing geometry that conforms to the geometry of adjacent endplate surfaces.

In any one of the embodiments, the first inner surface and second inner surface is configured to mate with the intermediate core, In some embodiments, the first outer surface is an articulating surface. In some embodiments, the second outer surface is an articulating surface. In some embodiments, both the first outer surface and the second outer surface are articulating surfaces.

In some embodiments, the first outer surface is a textured surface. In some embodiments, the second outer surface is a textured surface. In some embodiments, both the first outer surface and the second outer surface are textured surfaces.

In some embodiments, the first outer surface and second outer surface geometries are the same and comprise constant arcuate radii of curvature. In other embodiments, the first outer surface and second outer surface comprise different geometries. In still other embodiments, the first outer surface and second outer surface geometry are generally spherical.

In some embodiments, only the first outer surface geometry is generally spherical. In some embodiments, only the second outer surface geometry is generally flat with radiused edges. In others, the second outer surface geometry is generally flat near the center, transitioning to generally spherical near the radial edges. Still further, in some embodiments, the second outer surface geometry is generally flat and transitioning to a proportionately large spherical radius, to replicate a worn or surgically prepared endplate surface.

In any one of the embodiments, the first inner surface and the second inner surface are flat surfaces. In any one of the embodiments, the first inner surface and the second inner surface are concave surfaces. Still further, in any one of the embodiments, the first inner surface and the second inner surface are convex surfaces. Further still, in any one of the embodiments, the first inner surface and the second inner surface are non-flat surfaces.

In any of the aforementioned embodiments, the first inner surface and the second inner surface are textured surfaces, wherein the textured surface is surface configured to receive a fixation compound intended to bond an intermediate core to the implant.

In any one of the embodiments, the intermediate core is configured to be shock-absorbing and biocompatible. In some embodiments, the intermediate core is a hydrogel. In some embodiments, the intermediate core is a polymer.

In any one of the embodiments, the intermediate core upper surface is bonded to the first inner surface and the intermediate core lower surface is bonded the second inner surface, and the bond is permanent.

In any one of the embodiments, the first inner surface and the second inner surface are essentially parallel to each other about a central transverse plane.

In any one of the embodiments, the first endcap and second endcap are centered about a central axis. In addition, some embodiments further comprise the at least one protrusion centered about the central axis. In still other embodiments, the at least one protrusion is located off-center from the central axis.

In some embodiments, the first outer surface and second outer surface comprise slightly increasing arcuate radii of curvature from the outer radial edge surface to a zone near the central axis. Additionally, in some embodiments the first outer surface and second outer surface are inclined to each other about a central transverse plane to replicate the lordotic angle of the disc space. Alternately, in some embodiments, the superior and inferior surface of the intermediate core are inclined toward each other about a central transverse axis to replicate the lordotic angle. In still other embodiments, the arcuate radii of curvature of the first and second outer surfaces are essentially mirror images about a central transverse plane.

In some embodiments, the planar configuration of the implant is circular in shape about the central axis. In some embodiments, the planar configuration of the implant is elliptical in shape about the central axis. In still other embodiments, the planar configuration of the implant is a polygon in shape about the central axis. In some polygon configurations, the polygon comprises at least three edges, and preferable four or more side edges. In some embodiments the side edges are straight. In some polygon configurations, the polygon comprises an irregular polygon embodiment, wherein the side edges are curved, as in a Reuleaux polygon. In other irregular embodiments, the side edges are different lengths. In still other irregular polygon embodiments, the implant configuration may comprise any combination of number of sides, straight or curved edges and or length of individual edges.

In some embodiments, the implant comprises an anterior-posterior dimension that is greater than the overall arcuate height of the implant, wherein the ratio of the anterior-posterior dimension to the overall arcuate height is at least 1.01:1. In other embodiments, the ratio of the anterior-posterior dimension to the overall arcuate height is at least 1.1:1. In still other embodiments, the ratio of the anterior-posterior dimension to the overall arcuate height is at least 1.2:1. In still other embodiments, the ratio of the anterior-posterior dimension to the overall arcuate height is at least 1.5:1; or at least 2.0:1.

In some embodiments, the implant comprises a medial-lateral dimension that is greater than the overall arcuate height of the implant, wherein the ratio of the medial-lateral dimension to the overall arcuate height is at least 1.01:1. In other embodiments, the ratio of the medial-lateral dimension to the overall arcuate height is at least 1.1:1. In still other embodiments, the ratio of the medial-lateral dimension to the overall arcuate height is at least 1.2:1. In still other embodiments, the ratio of the medial-lateral dimension to the overall arcuate height is at least 1.5:1; at least 2.0:1, 3.0:1, or 4.0:1.

In some embodiments the implant comprises at least two protrusions. In other embodiments, the implant comprises exactly two protrusions. In some embodiments, the protrusions will be on different bearing surfaces. In other embodiments the protrusions will be on the same bearing surface. In some embodiments, the implant will have at least two protrusions on one bearing surface and at least one protrusion on another bearing surface.

In some embodiments, the implant comprises at least one conic protrusion on at least one bearing surface. In a preferred embodiment, the bearing surface will be an articulating surface.

Still further embodiments of the implant comprise two endcap bearing surfaces, the first endcap further comprises a first inner surface, and the second endcap comprises a second inner surface. Still further, in some embodiments, the first inner surface and the second inner surface each comprise a recessed cavity, thus creating a third inner surface (recessed area) and fourth inner surface (recessed area) on their inner surfaces respectively.

In matching configurations to the preceding embodiments, the intermediate core has a raised first surface and raised second surface, wherein the raised first surface of the intermediate core is configured to mate within the recessed cavity of the third inner surface of the first endcap, and the raised second surface is configured to mate within the recessed cavity of the fourth inner surface of the second endcap.

Still further, in an alternate (mirror-type) embodiment, the first inner surface of the first endcap and the second inner surface of the second endcap comprise a protruding third surface and fourth protruding surface respectively; wherein the intermediate core has a recessed cavity in the first surface and a recessed cavity is the second surface, and wherein the recessed surface of the first surface of the intermediate core is configured to mate with the protruding third surface of the first endcap, and the recessed cavity of the second surface of the intermediate core is configured to mate with the fourth raised surface of the second endcap.

In some embodiments, at least one of the first outer surface and the second outer surface is a bearing surface. Still further, in some embodiments, at least one of the first outer surface and the second outer surface is a polished bearing surface, wherein the at least one polished bearing surface has a surface finish ≤4 RMS. Further still, at least one of the first outer surface and the second outer surface is an articulating surface.

In some embodiments of the implant, exactly one of the bearing surfaces is an articulating surface and at least a portion of the opposite bearing surface is a textured surface. In some embodiments, at least a portion of one of the first bearing surface or second bearing surface is textured. In still other embodiments, at least a portion of both the first bearing surface and the second bearing surface is textured. Still further, in some embodiments, both the first outer surface and the second outer surface is a non-articulating surface and comprises more than one protrusion. In some of the preceding embodiments, the textured surface comprises more than one protrusion configured to contact a portion of at least one adjacent vertebral endplate.

In some of the preceding embodiments, at least a portion of the first outer surface or the second outer surface comprises a surface finish ≥125 RMS. In some embodiments, a surface comprising a surface finish ≥125 RMS is a textured surface. In some embodiments, a textured surface is a surface configured to receive a fixation compound. In some embodiments, a textured surface comprises a porous structure or porous coating, intended to mimic cancellous bone and to promote bone ingrowth.

In any one of the preceding embodiments, the implant is configured for use in the spine of a human, wherein the implant is a spinal disc implant.

In any one of the preceding embodiments, the implant is configured for use in the spine of a human, wherein the implant is a spinal fusion implant.

In any one of the preceding embodiments, the implant is configured for use in the spine of a human, wherein the implant comprises an articulating surface on one side and a fusion surface on the opposite side.

In any one of the preceding embodiments, the implant comprises a circular configuration in a In any one of the preceding embodiments, the implant is a unitary disc implant comprising no independent moving components.

In some of the preceding embodiments, the implant is a unitary disc implant comprising no independent moving components, as assembled.

In some embodiments, the implant described herein may be used in a joint, other than in the spine (of a human). In some embodiments, the implant is configured for use in an articulating joint. In other embodiments, the implant is configured for use in the spine of an animal. In still further embodiments, the implant is configured for use in a robotic articulating joint. In still further embodiments, any one of the preceding embodiments may be configured for (human) prosthetics.

Provided herein is another assembled implant adapted for placement between adjacent endplates of a vertebral joint comprising: a first endcap having a first outer surface and first inner surface, a first protruding attachment means, and an outer radial edge; a second endcap having a second outer surface and second inner surface, a second protruding attachment means configured to mate with the first protruding attachment means, and outer radial edge, an intermediate core having an upper surface and lower surface configured to mate between the first inner surface and the second inner surface, and further comprising a central opening configured to accommodate the first and second protruding attachments when assembled; at least one protrusion on at least one endcap surface, wherein the at least one protrusion is configured to contact a portion of at least one adjacent vertebral endplate.

In some embodiments, the first protruding attachment means is a protruding cylinder with a hole, centered about the central axis. In some embodiments, the first protruding attachment means is a protruding polygon having three or more sides with a hole, centered about the central axis. In some embodiments, the hole is a polygon having three or sides. Still further, in some embodiments, the hole may be a blind hole or a tapered hole. In some embodiments, the tapered hole comprises a Morse taper.

In some embodiments, the second protruding attachment means is a protruding cylinder with a hole, centered about the central axis. In some embodiments, the second protruding attachment means is a protruding polygon with a hole, centered about the central axis. In some embodiments, the hole is polygonal. Still further, in some embodiments, the hole may be a blind hole or a tapered hole. In some embodiments, the tapered hole comprises a Morse taper.

Still further, in some embodiments, the first protruding attachment means is a protruding cylinder, centered about the central axis. In some embodiments, the second protruding attachment means is a protruding polygon having three or more sides, centered about the central axis. In some embodiments, the second protruding attachment means is a protruding cylinder, centered about the central axis.

In some embodiments, the first outer surface is an articulating surface. In some embodiments, the second outer surface is an articulating surface. In still other embodiments, the first outer surface and second outer surface geometries are the same. Still further, in other embodiments, the first outer surface and second outer surface comprise different geometries.

In some embodiments, the first outer surface and second outer surface geometry are generally convex. In other embodiments, the first outer surface and second outer surface geometry are generally spherical. In still other embodiments, the first outer surface geometry is generally spherical. Still further, in other embodiments, the first outer surface geometry is generally spherical to convex. Yet in other embodiments, the first outer surface geometry is generally convex to spherical.

In some embodiments, the second outer surface geometry is generally flat. In other embodiments, the second outer surface geometry is generally flat to convex. Yet in other embodiments, the second outer surface geometry is generally flat and transitioning to a proportionately large spherical radius.

In some embodiments, the first inner surface and the second inner surface are flat surfaces. In some embodiments, the first inner surface and the second inner surface are concave surfaces. In some embodiments, the first inner surface and the second inner surface are convex surfaces. In still other embodiments, the first inner surface and the second inner surface are non-flat surfaces. In any one of the preceding embodiments the first inner surface and the second inner surface are textured surfaces. Still further, any one of textured surfaces is a surface configured to receive a fixation compound. Additionally, any one of textured surfaces is a porous coated surface configured to mimic cancellous bone and promote ingrowth.

In some embodiments, the intermediate core is configured to be shock-absorbing. Further, the intermediate core is biocompatible. Further still, the intermediate core may be a hydrogel or a polymer.

In any one of the preceding configurations, the first surface of the intermediate core is bonded to the first inner surface of the first endcap, and the second surface of the intermediate core is bonded the second inner surface of the second endcap. In any one of the preceding embodiments, the bond is permanent.

In some embodiments, the first outer surface and second outer surface are inclined to each other about a central transverse plane to replicate the lordotic angle of the disc space. Alternately, in some embodiments, the superior and inferior surface of the intermediate core are inclined toward each other about a central transverse axis to replicate the lordotic angle. In still other embodiments, the arcuate radii of curvature of the first and second outer surfaces are essentially mirror images about a central transverse plane.

In some embodiments, the first endcap and second endcap are centered about a central axis. In some embodiments, at least one protrusion is centered about the central axis. In some embodiments the at least one protrusion is located off-center from the central axis.

In still other embodiments, the first outer surface and second outer surface comprise slightly increasing arcuate radii of curvature from an outer radial edge surface to the central axis. Still further, in other embodiments, the first outer surface and second outer surface are essentially mirror images to each other about a central transverse plane.

In any one of the preceding embodiments, the planar configuration of the implant is circular in shape about the central axis. In any one of the preceding embodiments, the planar configuration of the implant is elliptical in shape about the central axis. Still further, in any one of the preceding embodiments, the planar configuration of the implant is polygonal in shape about the central axis, wherein the polygon comprises at least three side edges, and preferably four side edges. In any one of the preceding embodiments, the planar configuration of the implant comprises an irregular Reuleaux polygon. In any one of the preceding embodiments, the irregular Reuleaux polygon may comprise straight side edges, curved side edges or combinations of straight and curved side edges. Additionally, the lengths of the side edges need not be the same length.

In some embodiments, the implant comprises an anterior-posterior dimension that is greater than the overall arcuate height of the implant. In some embodiments, the ratio of the anterior-posterior dimension to the overall arcuate height is at least 1.01:1. In some embodiments, the ratio of the anterior-posterior dimension to the overall arcuate height is at least 1.1:1. In still other embodiments, the ratio of the anterior-posterior dimension to the overall arcuate height is at least 1.2:1. In still other embodiments, the ratio of the anterior-posterior dimension to the overall arcuate height is at least 1.5:1, or at least 2.0:1.

In some embodiments, the implant comprises a medial-lateral dimension that is greater than the overall arcuate height of the implant. In some embodiments, the ratio of the medial-lateral dimension to the overall arcuate height is at least 1.01:1. In other embodiments, the ratio of the medial-lateral dimension to the overall arcuate height is at least 1.1:1. In still other embodiments, the ratio of the medial-lateral dimension to the overall arcuate height is at least 1.2:1. In still other embodiments, the ratio of the medial-lateral dimension to the overall arcuate height is at least 1.5:1; at least 2.0:1, at least 3.0:1, or at least 4.0:1.

In some embodiments, the implant comprises at least two protrusions. In some embodiments, the implant comprises exactly two protrusions. In still other embodiments, the implant comprises at least one conic protrusion on at least one outer bearing surface. In some embodiments, at least one of the first outer surface and the second outer surface is an articulating bearing surface. In some embodiments, at least one of the first outer surface and the second outer surface is a polished articulating bearing surface. In some embodiments, the at least one polished articulating bearing surface has a surface finish ≤4 RMS.

In some embodiments, exactly one of the bearing surfaces is an articulating surface and at least a portion of the other of the surfaces is a textured surface. In some embodiments, at least a portion of at least one of the first outer surface and the second outer surface is textured. In some embodiments, at least a portion of both of the first outer surface and the second outer surface is textured. In still other embodiments, both of the first outer surface and the second outer surface is a non-articulating surface. Still further, in some embodiments, at least a portion of both of the first outer surface and the second outer surface is a fusion surface. In any one of the preceding embodiments, the textured, non-articulating or fusion surface may comprise more than one protrusion configured to contact a portion of at least one adjacent vertebral endplate. In any one of the preceding embodiments, the textured, non-articulating or fusion surface comprises a surface finish ≥125 RMS. In any one of the preceding embodiments, a textured surface is a surface configured to receive a fixation compound. In some embodiments, a textured surface comprises a porous structure or porous coating, intended to mimic cancellous bone and to promote bone ingrowth.

In any one of the preceding embodiments, the implant is configured for use in the spine of a human, wherein the implant is a spinal disc implant.

In any one of the preceding embodiments, the implant is configured for use in the spine of a human, wherein the implant is a spinal fusion implant.

In any one of the preceding embodiments, the implant is configured for use in the spine of a human, wherein the implant comprises an articulating surface on one side and a fusion surface on the opposite side.

In any one of the preceding embodiments, the implant is a unitary disc implant comprising no independent moving components.

In some of the preceding embodiments, the implant is a unitary disc implant comprising no independent moving components, as assembled.

In some embodiments, the implant described herein may be used in a joint, other than in the spine. In some embodiments, the implant is configured for use in an articulating joint. In other embodiments, the implant is configured for use in the spine of an animal. In still further embodiments, the implant is configured for use in a robotic articulating joint. In still further embodiments, any one of the preceding embodiments may be configured for prosthetics.

Provided herein is a unitary implant comprising at least one tether, configured for placement in the void of a conic feature. In other embodiments the implant further comprises at least one tether configured for placement in at least one fenestration.

In either of the immediately preceding configurations, the tether comprises at least one of: autologous tissue; allograft tissue; xenograft tissue; synthetic graft material; stem cells, chondrocytes; proteins; and/or growth promoting factors.

In still other configurations, the implant may further comprise an abutment on the second outer surface to restrict motion between the implant and the joint surface. In some embodiments, the abutment may comprise: a keel; a fin; a raised ridge; a post; or a spike. In still other embodiments the implant may comprise more than one abutment. In still other embodiments, the more than one abutment may be located on more than one bearing surface.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1 & 2 are representative side and isometric views of a discus-shaped, unitary implant having penetrating protrusions about the central axis.

FIG. 3 is a representative cross-sectional view of a discus-shaped, unitary implant comprising penetrating protrusions about the central axis, illustrating penetration of cartilage and or bony endplates of adjacent vertebral bodies.

FIGS. 4 & 5 are representative top (plan) and side views of the discus-shaped, unitary implant of FIG. 1, illustrating variable height options as measured about the arcuate height of the implant.

FIGS. 6 & 7 are representative top (plan) and side views of an elliptically shaped unitary discus implant having penetrating protrusions about the central axis on both surfaces, illustrating variable height options as measured about the arcuate height of the implant.

FIGS. 8 & 9 are representative top (plan) and side views, of an irregular polygon-shaped unitary implant, approximating the vertebral perimeter and having penetrating protrusions about the central axis, illustrating variable height options as measured about the arcuate height of the implant.

FIGS. 16-18 are representative top, cross-section and ISO views of an implant comprising a truncated conic protrusion on both surfaces, have a wider girth, and comprising a thru-hole, located on or about the central axis of the implant.

FIGS. 19-21 are representative top, cross-section and ISO views of an implant similar to one depicted in FIGS. 16-18, comprising a truncated conic protrusion on only one surface, have a wider girth, and comprising a blind hole, located on or about the central axis of the implant, which extends into the body of the implant but does not break through the opposite surface.

FIGS. 34-36 are representative isometric views of the implant similar to FIG. 33 illustrating alternate configurations comprising articulating, non-articulating and textured/fusion bearing surface combinations.

FIGS. 37-39 are representative section, plan and isometric views of a discus-shaped, unitary implant comprising a truncated conic protrusion about the central axis, with an optionally concentric central blind-hole. In addition, multiple anti-rotation protrusions are located on the same surface.

FIGS. 40-43 are representative A/P, side, bottom and isometric views of an irregular polygon-shaped (i.e.: Reuleaux polygon) unitary implant with a vertebral-approximating perimeter, comprising an elongated protruding rib or fin on one surface and a smooth opposite surface with no protrusions. The protruding fin is an alternative anti-rotation feature, preventing relative motion between the implant and the adjacent vertebral body.

FIGS. 44-47 are representative isometric views of FIG. 43 comprising alternative configurations of textured surfaces.

FIGS. 48-51 are representative plan, cross-section, ISO and exploded views of a discus-shaped, assembled unitary implant comprising an intermediate shock-absorbing core permanently bonded between the upper and lower discus-shaped endcap components.

FIGS. 52-55 are representative plan, cross-section, ISO and exploded views of a discus-shaped, assembled unitary implant comprising recesses in the implant end caps, with corresponding protruding sections on the intermediate shock absorbing core, permanently bonded between the upper and lower discus-shaped endcap components FIGS. 56-59 are representative plan, cross-section, ISO and exploded views of a discus-shaped, assembled unitary implant comprising end caps which employ a sliding fit mechanism to allow compressive axial movement, yet prevent lateral movement of one end cap relative to the other end cap. The shock absorbing core has a central through-hole. The surfaces of the shock absorbing core are permanently bonded to adjacently mating surfaces of the end caps.

FIGS. 60-62 are representative ISO views of salvage/fusion devices, comprising textured or bone-ingrowth promoting surfaces on both bearing endplate surfaces.

Figure 10:
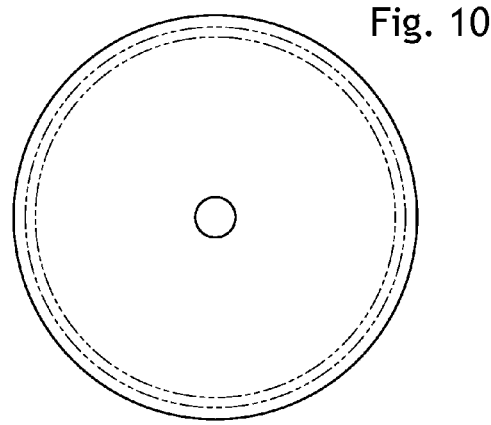
FIGS. 10 & 11 are top and side views of a representative variant of FIG. 4, illustrating variable lordosis (or kyphosis) of arcuate surfaces that are inclined relative to each other about a central Transverse plane, and represented by variable heights measured from the anterior and posterior sides of the implant.

These representative views are not intended as limiting representations. One skilled in the art would recognize that this implant could be fabricated in a wide variety of combination and configurations as illustrated herein, or from any number of recognized implantable materials, bone-ingrowth promoting surfaces, textures or coatings, or be configured similarly to any of the previously described shapes or configurations.

DETAILED DESCRIPTION OF THE INVENTION

The typical joint comprises two (and sometime three or more) mating bone end surfaces that are in close proximity or direct contact, each usually covered by and separated by a layer of hyaline cartilage and typically lubricated by natural joint synovial fluids. Structural classification names and divides joints according to the type of binding tissue that connects the bones to each other. There are three structural classifications of joints: fibrous joint—joined by dense regular connective tissue that is rich in collagen fibers: cartilaginous joint—joined by cartilage: and synovial joint—not directly joined—the bones have a synovial cavity and are united by the dense irregular connective tissue that forms the articular capsule that is normally associated with accessory ligaments.

Further, joints can also be classified functionally according to the type and degree of movement they allow; for example: Synarthrosis—permits little or no mobility. Most synarthrosis joints are fibrous joints (e.g., skull sutures): Amphiarthrosis—permits slight mobility. Most amphiarthrosis joints are cartilaginous joints (e.g., intervertebral discs): Diarthrosis—freely movable. All diarthrosis joints are synovial joints (e.g., shoulder, hip, elbow, knee, etc.), and the terms "diarthrosis" and "synovial joint" are considered equivalent by Terminologia Anatomica.

Diarthroses can in turn be classified into six groups according to the type of movement they allow: arthrodia, enarthrosis, ginglymus, rotary diarthrosis, condyloid articulation and articulation by reciprocal reception.

Joints can also be classified according to the number of axes of movement they allow, into mono-axial, biaxial and multi-axial. Still another classification is according to the degrees of freedom allowed, and distinguished between joints with one, two or three degrees of freedom. A further classification is according to the number and shapes of the articular surfaces: flat, concave and convex surfaces.

Joints can also be classified based on their anatomy or on their biomechanical properties. According to the anatomic classification, joints are subdivided into simple and compound, depending on the number of bones involved, and into complex and combination joints: Simple Joint: 2 articulation surfaces (e.g. shoulder joint, hip joint): Compound Joint: 3 or more articulation surfaces (e.g. radiocarpal joint), and: Complex Joint: 2 or more articulation surfaces and an articular disc or meniscus (e.g. knee joint).

Still further, the joints may be classified anatomically into the following groups: Articulations of hand; Elbow joints; Wrist joints; Axillary articulations; Sternoclavicular joints; Vertebral articulations; Temporomandibular joints; Sacroiliac joints; Hip joints; Knee joints; and Articulations of foot.

As defined herein, the term "unitary" shall mean, either an individual, single-component implant, or an implant comprised of more than one component, but having no internal moving parts or components, as assembled, wherein the implant performs as a single unit, or behaves as a single component. The intent of this description is to clarify that the implant component, or assembled components of this implant are not likely to generate intra-articular wear debris of its own making, or from its own core components, as a result of intra-component abrasion.

As defined herein, the term "adjacent joint surface" shall mean either, the naturally occurring state, or surgically prepared joint surface which is immediately adjacent to the surgically implanted device.

Provided herein is a unitary intervertebral device, comprising no independent moving components, for non-fusion articulation applications. The interbody articulating device allows for limited flexion and rotation between adjacent vertebrae, helping to preserve or restore near-normal motion between adjacent vertebrae. Rotational motion is achieved through one or more protrusions incorporated into the spinal interbody device. In one articulating form, a first protrusion extends perpendicularly from the superior aspect of the discus-shape of the interbody device forming a spike or rotational cone protrusion, while a second protrusion extends axially from the inferior aspect of the interbody device to form a second spike or rotational cone protrusion. In some embodiments, protrusions preferably extend perpendicularly from the apex of both the first and second arcuate articulating surfaces about the central axis. In another form, a single protrusion extends perpendicularly from the superior (first) aspect of a circular-shape of the interbody device to form a spike or anchoring protrusion, while the inferior (second) surface is slightly rounded and smooth. Alternately, the inferior surface comprises a textured or bone-ingrowth promoting surface. One or both of the first and/or second arcuate surfaces may be highly polished. Numerous planar geometries are described to define various profiles of the disc replacement implant which may be utilized, including irregular Reuleaux polygons. Numerous variations of the disc replacement are described. Similarly configured fusion salvage devices are also described.

In some embodiments, the implant is a joint implant, having applications in artificial limbs, robotics, or other joints and mechanisms. In some embodiments, the implant is a medical implant having applications for veterinary applications intended to repair or replace a joint in an animal. In still other preferred embodiments, the implant is a human medical implant intended for a complex cartilaginous joint of the spine (intervertebral disc).

Figure 14:
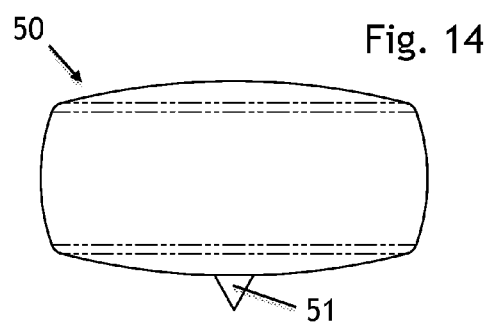
FIG. 14 is a side profile view of a discus-shaped, unitary implant variation, similar to that depicted in FIG. 1, comprising a penetrating protrusions about the central axis on just one surface.
Figure 15:
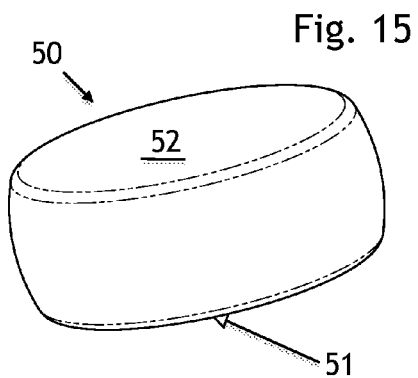
FIG. 15 is an isometric view of the implant shown in FIG. 14 illustrating an embodiment with a smooth bearing surface.

Provided herein is a unitary implant adapted for placement between adjacent surfaces of a joint comprising: a first bearing surface and a second bearing surface, wherein the first and second bearing surfaces are generally convex and configured to have bearing surface curvature that generally conforms to the concave geometry of the adjacent joint surfaces; an outer radial edge surface; and a first protrusion on the first bearing surface, as illustrated in FIG. 14 or 15, wherein the first protrusion is configured to contact a central portion of a first adjacent joint surface, and wherein the first protrusion is adapted to allow rotation about an axis.

As defined herein, convex shall be construed to mean: having an outline or surface curved like the exterior of a circle or sphere.

In some embodiments, the unitary implant further comprises a second protrusion on the second bearing surface, as illustrated in any one of FIG. 1-3, 5, 7, 9, 11, or 13, wherein the second protrusion is configured to contact a central portion of a second adjacent surface, and wherein the second protrusion is adapted to allow rotation about the common axis of the first and second protrusions.

In some embodiments of the unitary implant the first protrusion is conical. In some embodiments, the second protrusion is conical. In still other embodiments, the first protrusion or second protrusion may comprise a cone, a curved cone (sometimes referred to as parabolic or hyperbolic cones), a truncated cone, or a cylinder. In other words, the protrusion may comprise any appropriate shape that would facilitate rotation, when placed about a central, rotational axis. In some embodiments, the protrusions are different on opposite surfaces. As illustrated in FIG. 3, the protrusions would intentionally penetrate the existing (or remaining) cartilage on the adjacent endplates of a joint, and at least minimally penetrate the boney endplate at or about the approximate center of rotation of the joint to stabilize the implant.

Accordingly, an illustrative intervertebral disc prosthesis 10 as represented by FIGS. 1-3 is a unitary (single component), symmetric, discus-shaped device having highly polished, gradually curving superior and inferior surfaces 11 and 12 with slightly increasing arcuate geometry from the peripheral blended edges 16 and 17 to the central axis W, culminating in protrusions 13 and 14 about the central axis on both the superior 11 and inferior 12 surfaces. The sidewalls of the disc implant 15 transition smoothly with blended edges 16 and 17.

The terms "superior" and "inferior" are used herein with reference to the orientation of the disc 10 when it is implanted in the human body wherein the head is superior to the feet and the feet are inferior to the head on an erect spine of the human body. Other paired terms having similar meaning in this specification include; "upper" or "cephalad", (meaning toward the head); and "lower" and "caudal" or "caudad" (meaning toward the tail or feet, and away from the head).

The protrusions 13 and 14 extending from the superior 11 and inferior 12 surfaces respectively, engage the adjacent cephalad 18 and caudal 19 vertebra respectively, piercing any remaining cartilage on the endplates 20 and 21 in the approximate central region of their respective bearing surfaces, to retain the disc prosthesis in position between the vertebra as shown in FIG. 3. Advantageously, any remaining cartilage on the endplates 20 and 21 would be beneficial to the highly polished surface(s) and protrusion(s), promoting improved rotational properties for the implant about the protrusions. Additionally, over time, any minor variations between the cartilage bearing surfaces would naturally conform to the approximately similar radial geometry of the implant bearing surfaces, minimizing or completely eliminating the need to surgically prepare the endplate surface to match the implant.

The penetrating protrusions 13 or 14 can be any surface of revolution about the central axis W where the base is broader than the tip. The acute end of the tip protrusion may be pointed or slightly rounded. Similarly, the protrusion may have a base of any geometry projected to the tip or apex of any geometry as long as it is smaller than the base. Preferably, in this configuration, the protrusion would be configured to promote rotation about the central axis W, meaning, the protrusion(s) would be circular in nature having a single axis of rotation.

The penetrating protrusion tips 13 and 14 would intentionally penetrate, at least minimally, into the approximate articulating center of the superior and inferior cartilaginous covered endplates 20 and 21, or debrided bony endplates, as illustrated in FIG. 3. The penetrating protrusion would have the purpose of providing a pseudo anchor, or spatial immobilizing member for the device, to position and prevent migration or expulsion of the implant during flexion/extension of the vertebral column. Additionally, in the case where the penetrating protrusions comprise a singular axis of revolution on the articulating surface of the implant, they would also serve as the axis of rotation between the implant and the adjacent vertebral body. Height of the protrusions can typically range from 0.3 mm to 2.5 mm.

The penetrating protrusions may also act as microfracture point(s) for the vertebral endplates. There is significant documentation in the literature that demonstrates how the human vertebral endplates will tend to calcify resulting in the early stages of disc degeneration, as early as age 25.

The vertebral endplates are identifiable from an early embryological stage, and have an osseous as well as a hyaline cartilage component. The cartilaginous component generates interest since it persists throughout normal maturation while the adjacent vertebrae undergo ossification. It comprises a gel of hydrated proteoglycan molecules reinforced by a network of collagen fibrils. Unlike the articular cartilage of the synovial joints, the collagen fibrils do not connect the endplate directly to the vertebral bone, although the endplate does have intimate contact with the disc through the lamellae of the inner annulus. A network of microscopic blood vessels penetrates the endplates during development of the growing spine, principally to provide nutrition for the disc, before disappearing around the time of skeletal maturity (i.e.: ossification). Apart from a sparse vascular supply in the outer lamellae of the annulus, mature discs are almost totally reliant on diffusion of essential solutes across the endplates for nutrition and metabolic exchange. Once ossification of the endplates occurs, no further direct nutrition is received by the endplate cartilage from the vertebral marrow, limiting its ability for self-repair.

Proteoglycan molecules within the matrix are critical for the control of solute transport and maintenance of water content in particular throughout the disc, and depletion of proteoglycans from the endplate cartilage is associated with loss of proteoglycans from the nucleus. It follows therefore that proteoglycan loss would ultimately lead to degeneration of the disc and endplate cartilage. Upon reaching skeletal maturity the cartilage of the endplate undergoes substantial remodeling, resulting in extensive mineralization which is eventually resorbed and replaced by true bone. Importantly, this new tissue most likely impedes the hitherto critical diffusion and nutrient exchange between the vertebral marrow, endplate cartilage and the disc. The small blood vessels within the endplate likewise become obliterated by this calcification, further limiting the exchange of vital nutrients.

Perhaps surprisingly, the endplate can become re-vascularized after maturity in some species under normal and pathological conditions. In at least one sheep study, the re-vascularization, presumed to be an attempt at tissue repair, was not able to reverse the inevitable cascade of degeneration caused by annular disruption. However, the creation of blood vessels in the endplate occurred by activation of the matrix degrading metalloproteinase (MMP) enzymes which are normally maintained in a latent form by tissue inhibitors.

The human spine may have similar regenerative potential to repair, or at least lubricate the cartilaginous endplate near the protruding point of fixation 13, 14 for the artificial disc, in a manner similar to the ends of long bones with synovial joints as has been previously demonstrated by micro-fracturing techniques. Specifically, in addition to providing a rotation anchor, the penetrating protrusion tip(s) would cause the equivalent of a microfracture to the vertebral endplate resulting in a natural repair response from the vertebra in the form of vascular micro-vessels forming in and around the penetration point. The micro-vessels would provide a means for supplying regenerative blood supply and nutrients from the vertebral marrow through the otherwise calcified endplate structure of the vertebral body to the cartilage. Alterations in the ossified endplates, due to the microfracture effects of the penetrating protrusions would provide a renewed source of blood, stem cells and nutrients from the vertebral bodies and would likely result in reformation of a pseudo-cartilage or fibrocartilage around the protrusions.

As has been shown in the human knee, this natural response from microfracture will frequently lead to the formation of cartilage-like repair tissue, sometimes referred to as fibrocartilage, often with a mixture of hyaline cartilage formed within and around the periphery of the fibrocartilage. Although not as strong or durable as hyaline cartilage, the fibrocartilage still provides a better cushion and articulation surface than bone itself. When this fibrocartilage response is duplicated around the penetrating protrusions tip(s) of the discuss implant, it will serve as a bridging material between the endplate, and the remaining native cartilage on the endplate, providing an excellent articulating area for the implant.

Still further, the first protrusion or second protrusion may comprise a truncated cone with a hole about the central axis, or a cylinder with a hole about the central axis. Still further, the hole in the protrusion may be a blind hole or a thru-hole that penetrates through the entire implant, as illustrated in FIGS. 16-21.

In some embodiments, the implant comprises a truncated cone with a hole about the central axis, or a cylinder with a hole about the central axis, the implant may also comprise a tethering feature that is configured to promote ingrowth or attachment to the adjacent vertebra, as illustrated in FIGS. 22-27. In some embodiments, the attachment may be to just one adjacent endplate or vertebra. In other configurations, the attachment may be to both of the adjacent endplates or vertebrae. Such a tethered configuration would provide for a unique implant design that would promote a new form of pseudo-ligamentous fixation between the adjacent vertebrae, having either polished, articular bearing surfaces, fusion surfaces, or both. In the case where there is an articular bearing surface coupled with a tether, the combined interface would potentially allow for limited rotation, where the tether would act as a substitute for native spinal ligamentous tissues.

In some embodiments, the first protrusion and/or the second protrusion is adapted to penetrate at least the cartilage of the first adjacent joint surface and/or the second adjacent surface providing an extremely conservative surgical procedure. As illustrated by FIGS. 1-13, no special articular endplate preparation would be required to insert the implant and obtain cartilage and/or at last partial endplate penetration with the protrusion(s). In other embodiments, a first protrusion only is adapted to penetrate the endplate of a first adjacent joint surface only, as illustrated by FIGS. 14 and 15.

In other embodiments of the unitary implant, the implant may comprising a polished first bearing surface, with no protrusions, and further may comprise at least a first and second (or more protrusions) on the second bearing surface as illustrated in FIGS. 31-35, wherein the at least first and second protrusion are configured to contact a portion of a second adjacent surface, preferably penetrating at least a portion of the adjacent endplate, and wherein the at least first and second protrusion are adapted to prevent movement between the second bearing surface and the second adjacent surface. Alternately, this configuration may also comprise a textured surface in addition to the protrusions, to further promote boney or fibro-cartilage attachment between the implant and the adjacent endplate, as illustrated in FIG. 36.

Figure 28:
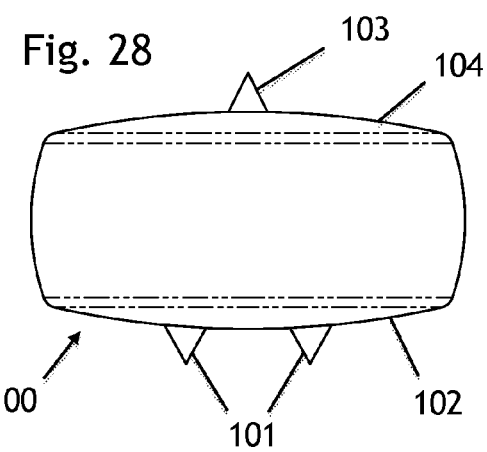
FIGS. 28-30 are representative side, bottom and ISO views of a discus-shaped, unitary implant having a single penetrating protrusion about the central axis on one surface and multiple protrusions on the opposite surface.
Figure 31:
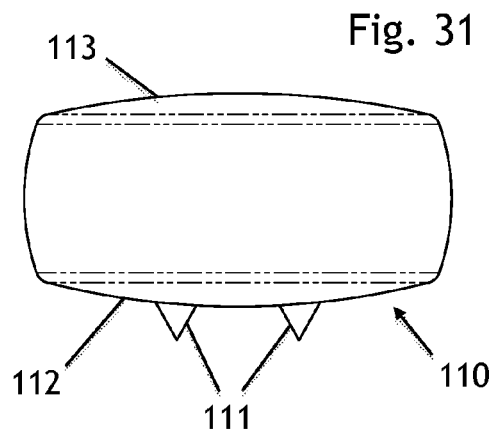
FIGS. 31-33 are representative side, bottom and isometric views of a discus-shaped, unitary implant having multiple penetrating protrusion on one surface and no protrusions on the opposite surface.
Figure 29:
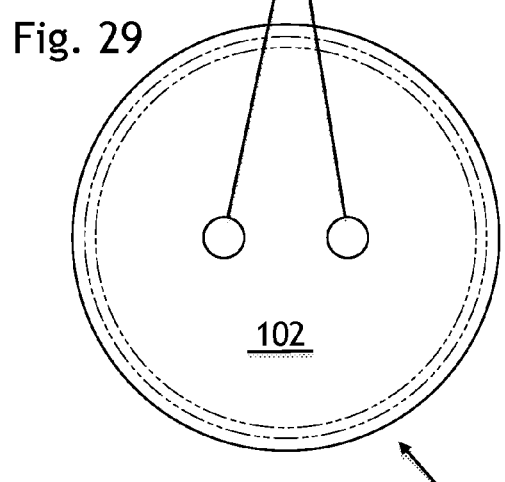
Figure 32:
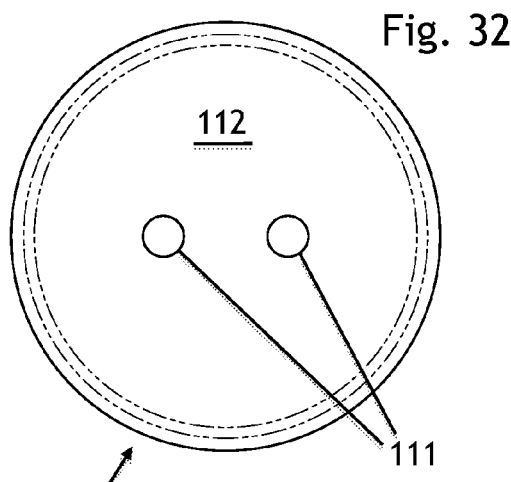
Figure 30:
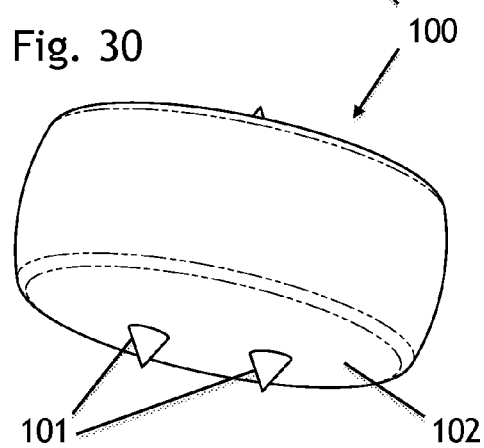
Figure 33:
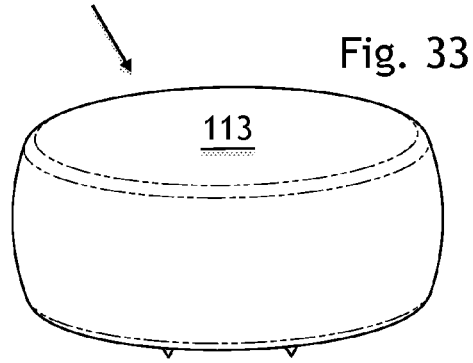
Figure 62:
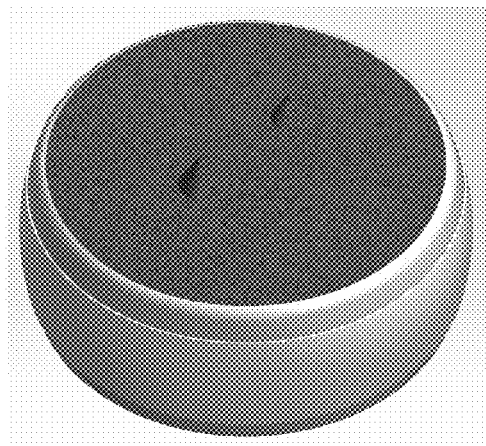

In still other embodiments of the unitary implant comprising a first protrusion on the first bearing surface, the implant may comprise at least a second and third protrusion on the second bearing surface as illustrated in FIGS. 28-30, wherein the at least second and third protrusion are configured to contact a portion of a second adjacent surface, preferably penetrating at least a portion of the adjacent endplate, and wherein the at least second and third protrusion are adapted to prevent movement between the second bearing surface and the second adjacent surface.

In some embodiments of the unitary implant, the implant is generally circular in shape 10 about a central axis (i.e.: FIG. 4) comprising a circular perimeter 22. In other embodiments, the implant is non-circular, polygonal or irregular polygonal in shape, 30, 40 about a central axis. In certain preferred embodiments, the implant comprises an elliptical planar shape or a common variant thereof. Various non-limiting illustrations of such configurations are illustrated in FIGS. 4, 6 and 8.

As defined herein, "elliptical" shall mean a curve on a plane surrounding two focal points such that a straight line drawn from one of the focal points to any point on the curve and then back to the other focal point has the same length for every point on the curve. As such, it is a generalization of a circle which is a special type of an ellipse that has both focal points at the same location, as illustrated by the non-limiting example of FIG. 6 having an elliptical perimeter 31. The shape of an ellipse is represented by its eccentricity which for an ellipse can be any number from 0, (the limiting case of a circle), to arbitrarily close to, but less than 1. Alternatively, the elliptical shape may be defined as an irregular ellipse, wherein curve on a plane surrounding two focal points such that a straight line drawn from one of the focal points to any point on the curve and then back to the other focal point has the similar, but variable lengths for every point on the curve.

Still further, in other preferred embodiments, the implant shape may resemble a Reuleaux polygon planar shape comprising three or more sides. The Reuleaux polygon shape 40 may be in the form of an irregular polygon, wherein at least one or more sides of the polygon are straight, or wherein at least one side has a different length than the remaining sides. Still further the Reuleaux polygon shape may be in the form of an irregular Reuleaux polygon, wherein at least one or more sides of the polygon are curved 41, or wherein at least one (curved) side has a different length than the remaining sides, as illustrated by the non-limiting examples of FIGS. 8, 12, and 40-47. Still further the Reuleaux polygon shape may have a combination of straight and curved sides.

In some embodiments, the implant comprises an anatomic-like bearing surface, wherein the curvature of the first bearing surface 11, 33, 43 and the second bearing surface 12, 34, 44 is generally spherical or near spherical. The geometry of these bearing surfaces can either be a surface of revolution about a center axis W, as represented by surfaces 11 and 12 in implant 10; or they can be any swept surface as represent by surfaces 33, 34, 43 and 44 in implants 30 and 40 or a lofted surface. A swept surface is defined as the geometry resulting from a sectional curve following a path of another curve. A lofted surface is defined as the surface geometry formed by a matrix of varying section curves in one direction along with varying section curves in another direction where the direction of the two sets of curves are different from each other. Typically, the direction of the curves are normal to each other, but do not need to be.

In other embodiments, the curvature of the first bearing surface and the second bearing surface is generally multi-radial in order to more closely match the native or prepared endplate surface. In still other embodiments, the first bearing surface and the second bearing surface geometries are the same. Alternatively, in other embodiments, the first bearing surface and the second bearing surface comprise different geometries.

Still further, in some embodiments the first bearing surface and the second bearing surface are mirrored, or symmetrical about a central transverse plane, wherein the overall arcuate height 23, 32, and 43 is constant, as illustrated in the non-limiting examples of FIGS. 5, 7 and 9.

Figure 11:
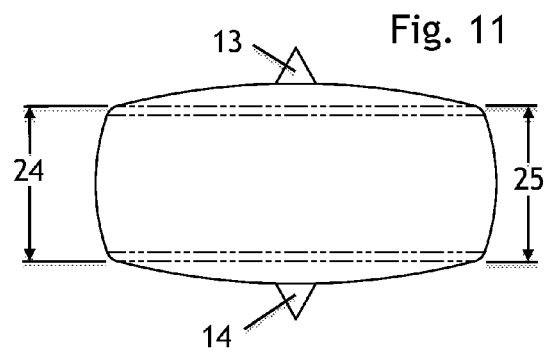
Figure 13:
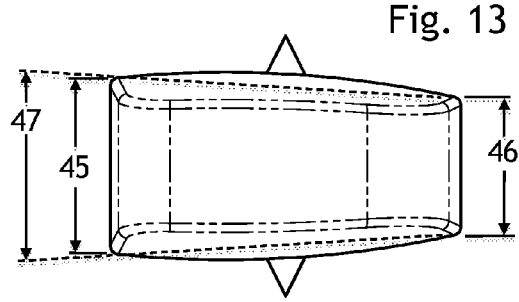

In other embodiments, the first bearing surface and the second bearing surface are inclined to each other about a central transverse plane to better match or reconstruct the natural curvature or lordosis and kyphosis of the spine, as illustrated in the non-limiting examples of FIGS. 11 and 13.

In cervical and lumbar applications, the angle of inclination of the superior surface relative to the inferior surface is commonly referred to as the lordotic angle, and typically ranges between 0.1 and 20 degrees, or more particularly between 4 and 15 degrees. (However, in some cases this angle may be as high as 25 degrees). As illustrated in FIG. 13, the lordotic angle 47 is such that the height on the anterior surface 45 is almost always greater than the posterior surface 46. As further illustrated by FIG. 11, the lordosis or inclination angle between the first and second bearing surfaces may also be directly implied by describing an implant with different anterior 24 and posterior 25 dimensions. In the thoracic spine, the angle of inclination is referred to as a kyphotic angle, the opposite of lordosis.

In some embodiments of the implant, the first bearing surface and the first protrusion are polished articulating surfaces as illustrated in the non-limiting examples of FIGS. 28 and 29. In other embodiments, the second bearing surface and the second protrusion are polished articulating surfaces as illustrated in the non-limiting examples of FIGS. 14 and 15. In this embodiment 50, the central protrusion 51, resides on only one surface of the implant verses protrusions 13 and 14 on both surfaces (FIG. 11). Typically this protrusion would be on the inferior surface. However, it could also be located on the superior surface. The surface 52 opposite the surface with the protrusion 51 is sufficiently smooth and polished in order to articulate against the native cartilage or endplate, while minimizing wear. This embodiment of one central protrusion on either the inferior or superior surface, but not both, can be incorporated with any of the previously mentioned perimeter geometries (22, 31 and 41) with superior and inferior surfaces positioned either approximately parallel to each other (FIG. 11) when viewed perpendicular to the coronal plane or at a lordotic angle 47, (FIG. 13).

In still others, all of the bearing surfaces and protrusions are polished articulating surfaces, as illustrated in the non-limiting examples of FIGS. 1-13.

In any one of the embodiments described herein, the first bearing surface or second bearing surface may comprise or be manufactured from at least one of the following materials: pyrolytic carbon, titanium, titanium nitride, tantalum, cobalt, chromium, polyethylene, PEEK® (Polyether ether ketone), Delrin®, alumina, zirconia, silicon carbide, silicon nitride, stainless steel, diamond, or a diamond like material. In some embodiments, the unitary implant may comprise a core fabricated from one material having one set of properties, and an outer bearing surface fabricated from another material having a different set of properties. As a non-limiting example, a pyrolytic carbon implant may have a graphite core and a pyrolytic carbon exterior for bearing surfaces. Alternatively, an implant may have a first bearing surface with one set of material properties (i.e. low abrasion articulating surface), and a second bearing surface comprising different material properties (i.e.: fixation promoting surface), and an intermediate core comprising yet a third set of material properties (dampening, shock-absorbing properties).

Provided herein is a unitary disc implant adapted for placement between adjacent vertebral surfaces of a spinal joint comprising: a first bearing surface and a second bearing surface, wherein the first and second bearing surfaces are generally convex and configured to have curvature that generally conforms to the concave geometry of the adjacent spinal joint surfaces; an outer radial edge surface; a first protrusion on the first bearing surface, wherein the first protrusion is configured to contact a central portion of a first adjacent spinal joint surface, a second protrusion on the second bearing surface, wherein the second protrusion is configured to contact a central portion of a second adjacent spinal surface, wherein the first protrusion and second protrusion are adapted to allow rotation about an axis, as illustrated in FIGS. 1-13, 16-18 and 48-58.

Provided herein is a unitary spinal disc implant adapted for placement between adjacent vertebral endplates comprising: a first bearing surface and an second bearing surface, wherein the first and second bearing surfaces are generally convex and configured to have a spherical curvature geometry that conforms to the concave geometry of adjacent endplate surfaces; an outer radial edge surface that blends into the first and the second bearing surfaces; a conic protrusion on at least one bearing surface for penetrating at least one of the adjacent endplates, wherein the conic protrusion is configured to contact a central portion of at least one adjacent vertebral endplate, as illustrated in FIGS. 14, 15, and 19-21.

In some embodiments, the first bearing surface is an articulating surface. In some embodiments, the second bearing surface is an articulating surface. In some embodiments, the first bearing surface and second bearing surface geometries are the same. In some embodiments, the first bearing surface and second bearing surface comprise different geometries, with such differences as illustrated between FIGS. 34 and 36 or the superior surface of FIG. 42 and the inferior surfaces of FIGS. 44-48.

In some embodiments, the first bearing surface and second bearing surface geometry are generally convex. In some embodiments, the geometry of the first bearing surface and/or second bearing surface is generally spherical. In some embodiments the first bearing surface geometry is generally flat to spherical.

In still other embodiments, only the second bearing surface geometry is generally flat to spherical. Alternately the second bearing surface geometry may be generally flat with radiused edges. Still further the second bearing surface geometry may be generally flat and transitioning to a proportionately large spherical radius to replicate a worn or surgically prepared endplate surface. Such variations in the second bearing surface, (typically the inferior surface), would be advantageous when addressing the surgical desire to match or closely replicate a surface that is either severely abraded due to (compressive) arthritic wear, or a surface that is surgically scraped by the surgeon to remove osteophytes, and disrupted or torn cartilage, resulting in a less than natural radius of curvature on this surface which might otherwise interfere with the function of the implant. One skilled in the art will also recognize that the inferior is often easier for surgeon to access with instruments, depending on the surgical approach used.

In even further embodiments, the first bearing surface and second bearing surface comprise slightly increasing arcuate radii of curvature from the outer radial edge surface to the central axis. In some embodiments, the arcuate radii of curvature of the first and second bearing surfaces are essentially mirror imaged about a central transverse plane.

By way of example, in any one of the embodiments described herein, the radius of curvature R of the endcap is calculated by the formula: $R=H/2+W^2/8H$; wherein H is the height of the arc of the implant; W is the width of the implant (in either the sagittal or coronal plane).

In any of the embodiments described herein the width of the implant or chord of the arc, (in either the sagittal or coronal plane) has a range between 17.0 mm and 69.0 mm, whereas the height of the spherical radius of curvature of the of the bearing surface comprises a range between 0.1 mm (generally flat) and 5.0 mm.

In addition, the spherical radius can be variable within the full spectrum of these ranges, in both planes simultaneously, meaning that a given bearing surface can have more than one spherical radius at any given measurement point. Ideally, for manufacturing purposes, the spherical radii would be nearly constant for the majority of the surface area (i.e.: >60%) in any one axis, before blending to the radial edges. However, the inventors recognize that the spherical radius may be customized to better accommodate different spherical radii of the endplate surface near the center of the endplate versus the spherical radius near the perimeter of the endplate (the epiphyseal rim), accounting for central endplate wear, abrasion or surgical preparation, as may be typically seen on the inferior endplate. Customized, variable spherical radii can now readily be achieved in manufacturing processes that utilize CNC multi-axis machining centers.

The differences between the spherical curvatures in the sagittal and coronal planes would be further exaggerate in an ideally elliptical shaped or irregular Reuleaux polygon shaped implant, wherein the anterior-to-posterior width of the device would be narrower than the medial-to-lateral width, potentially requiring a larger coronal spherical radius and narrower sagittal spherical radius.

To further illustrate the variability of the geometry in some embodiments, the second outer surface geometry is generally flat with radiused edges. In others, the second outer surface geometry is generally flat to convex. Still further, in some embodiments, the second outer surface geometry is generally flat and transitioning to a proportionately large spherical radius, as described above, to replicate a worn or surgically prepared endplate surface, typically representing the inferior endplate in a spinal joint.

As used herein, the anatomic body planes are the imaginary flat surfaces that are used to define a particular area of anatomy. The most common ones being: The Frontal or Coronal Plane which vertically divides the front and back halves of the entire body; The Median, Midsagittal or Sagittal Plane—which vertically divides the left and right sides of the entire body; and The Transverse or Horizontal Plane—which divides the body (horizontal to the ground) at the waist (top and bottom halves of the body). In this specification, the terms are applied universally to any bone in the spine.

In some embodiments, the first bearing surface and second bearing surface are centered about a central axis, wherein the implant surfaces are essentially symmetric about both the coronal and sagittal planes. Further still, the at least one conic protrusion is centered about the central axis. In other embodiments, the at least one conic protrusion is located off-center from the central axis. An example of this can be seen in FIGS. 28-30.

Still further, in some embodiments, the implant comprises an anterior-posterior (front to back) dimension that is greater than the overall arcuate height of the implant. This dimensional configuration can be provided in a range and may be represented by a ratio wherein the anterior-posterior dimension to the overall arcuate height is at least 1.01:1; is at least 1.1:1; or is at least 1.2:1, etc., for non-limiting example, as illustrated in FIGS. 4 and 5, 6 and 7, or 8 and 9.

Further still, in some embodiments, the implant comprises a medial-lateral dimension that is greater than the overall arcuate height of the implant. This dimensional configuration can also be provided in a range and may be represented by a ratio wherein the medial-lateral dimension to the overall arcuate height is at least 1.01:1; is at least 1.1:1; is at least 1.2:1, etc., for non-limiting example.

In some embodiments, the implant comprises at least two protrusions. In other embodiments, the implant comprises exactly two protrusions. In still other embodiments, the implant comprises at least one protrusion on at least one bearing surface, wherein the at least one protrusion is conic.

Still further, in some embodiments, the at least one conic protrusion is a truncated cone 61, 62, 71 comprising a base diameter 64, 65 with a wider girth at the base than the top 66, 67 and may further comprise an inner void 63, 72 as illustrated in any of the non-limiting examples of FIGS. 16-27. In those embodiments where the conic protrusion includes an inner void, the void may be a blind hole 73, 74, or it may be a void that extends through the entire implant 63. In preferred embodiments the conic protrusions, and holes or voids would be concentric about a central axis. In other embodiments neither the conic protrusions nor voids would be concentric, or centered about a central axis.

Referring now to FIGS. 16-18, an embodiment 60, comprises truncated conic protrusions 61 and 62 respectively located at the center or the approximate center of superior and inferior surfaces 68, 69 respectively, similar to protrusions 13 and 14 (FIG. 1) except that they have a larger base perimeter (64, 65) and truncated top (66, 67) to accommodate a thru-hole 63 sized to allow for bone or tissues ingrowth, or graft material that is intended to provide additional capture, further minimizing the potential for expulsion. The perimeter or cross section geometry of the thru-hole can either be a circle, preferred for manufacturing reasons, or any other geometry. The size of the thru-hole 63 is a size that accommodates and promotes bone or tissue ingrowth. This size, generally, will typically have a sectional area range equivalent to diameters ranging from 2.0 mm to 10.0 mm, but may be larger or smaller. The surface finish of the thru-hole 63 may be textured to provide better adhesion properties for ingrowth of tissue. A surgeon may decide to fill this through hole with harvested bone chips or synthetic bone (or other graft material) with or without bone growth stimulators.

Another embodiment 70, represented by FIGS. 19-21, comprises a protrusion 71 with a blind hole 72 on just one surface 75 that can be either the superior or inferior surface of the implant. The geometry of the protrusion is similar to 61 and 62 previously mentioned (FIG. 17) and the average sectional width 73 of blind hole 72 is similar to previously mentioned thru-hole 63. The depth 74 of the blind hole may at a minimum be about 0.5 mm, and at a maximum depth being approximately 1.0 mm from the point of breaking through the opposite surface 76. The surface finish of the blind hole 72 may be textured to provide better adhesion properties for ingrowth of tissue. Additionally, the hole may be inversely tapered to promote a better anchoring reservoir that would resist pullout of the anchoring materials under natural loading conditions. This embodiment can be incorporated with any of the previously mentioned perimeter geometries (22, 31 and 41) with superior and inferior surfaces positioned either approximately parallel to each other when viewed perpendicular to the coronal plane, or at a lordotic angle 47. A surgeon may decide to fill this blind hole with harvested bone chips or synthetic bone (graft material) with or without bone growth stimulators.

Figure 22:
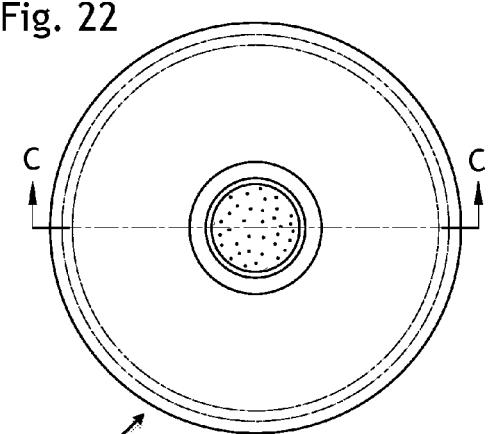
FIGS. 22-24 are representative top, cross-section and ISO views of an implant similar to one depicted in FIGS. 16-18 and comprising a biocompatible tether or wick-tethering device.
Figure 25:
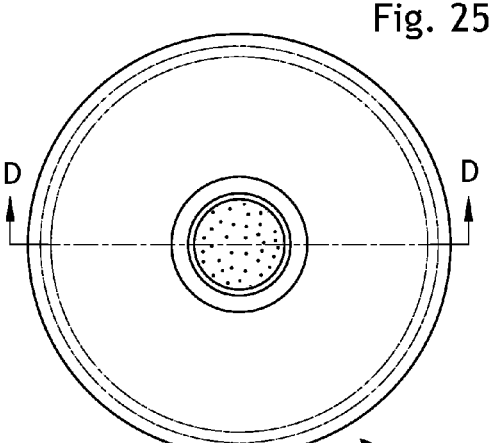
FIGS. 25-27 are representative top, cross-section and side views of an implant similar to one depicted in FIGS. 19-21 and comprising a biocompatible tether or wick-tethering device.
Figure 23:
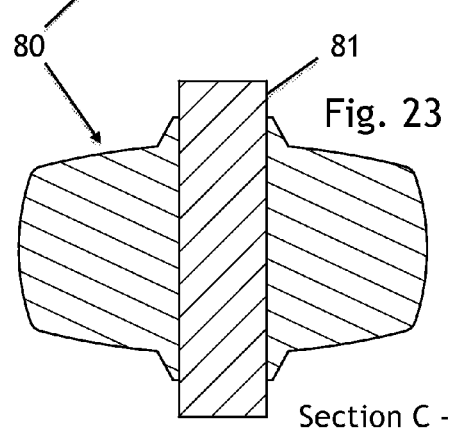
Figure 26:
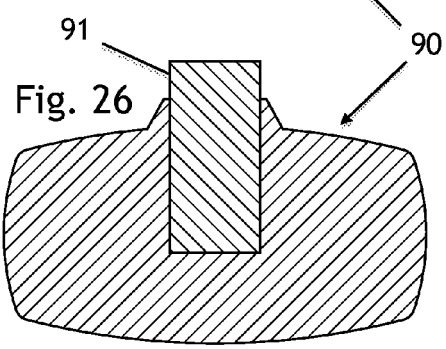
Figure 24:
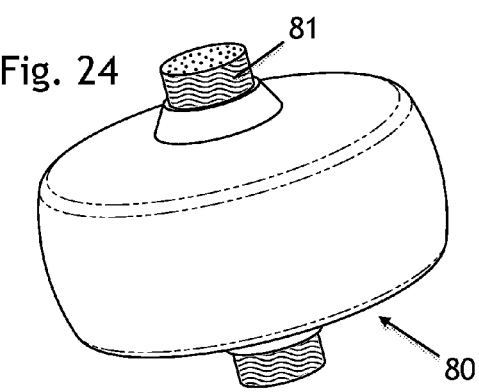
Figure 27:
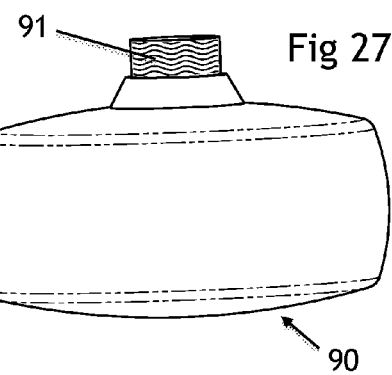

Referring now to FIGS. 22-24, embodiment of the invention 80, illustrates one example of the previous illustration wherein a surgeon can utilize a biocompatible tether or wicking tether 81. Likewise, implant 90, shown in FIGS. 25-27 illustrates another example where the blind hole 72 contains a biocompatible tether or wicking tether 91. The biocompatible "wick" or "tethering" devices 81 and 91 function in a fashion similar to an artificial ligament, by promoting growth of new tissue between the disc implant and the adjacent vertebral body(s) creating an additional stabilizing structure for the spinal joint segment. The surface finish of the blind hole may be textured to provide better adhesion properties for ingrowth of tissue. Additionally, the hole may be inversely tapered to promote a better anchoring reservoir that would resist pullout of the anchoring materials under natural loading conditions. Alternatively, the tether could be cross-pinned (not shown) through the side wall of the implant to fix it within the implant. The tethers 81 and 91 could be fabricated from any number of materials, including autologous tissues, allograft tissues, xenografts tissues, or a variety of artificial, man-made synthetic graft materials. These materials could also be impregnated or treated with stem cells, chondrocytes, proteins or other growth promoting factors to further the likelihood of a successful graft.

Referring now to FIGS. 28-30, another embodiment 100 of the invention is similar to discs 10, 30, and 40 except there are two or more protrusions 101 on one bearing surface 102, that can either be the inferior surface or the superior surface, as well as one protrusion 103 on the other surface 104. This embodiment is designed to allow articulation on only one side of a vertebral joint; against the surface 104, having only one protrusion 103. The multiple protrusions 101, each of which shaped as previous defined protrusions 13 and 14, can be located anywhere on the surface 102 and are intended to prevent this surface 102 from moving relative to the adjacent vertebral endplate (as depicted in FIG. 3-20 or 21). One of the protrusions 101 can be located at the center of surface 102 with one or more protrusions located off center. Or all of the protrusions can be located in areas other than the center of surface 102.

Alternatively, referring now to FIGS. 31-35, embodiment 110 is similar to that depicted by 100 except that there are no protrusions on surface 113. The surface 113 is similar to previously defined articulating surface 52. Still further, another embodiment 120 (FIG. 36), comprises a roughened, coated or porous surface 122. Surface roughness, (such as grit blasted, textured, porous, laser sintered, roughened porous spray titanium or as coated pyrolytic carbon); coatings (such as Hydroxyapatite); porous coating (such as porous titanium, tantalum or silicon nitride); or porous formation (such as chemical etching of the surface); on the bearing surface(s) are meant to promote fibrous or bony on-growth and/or ingrowth as a means of further anchoring the device. These surface treatments are those commonly known to the industry and one skilled in the art.

Figure 12:
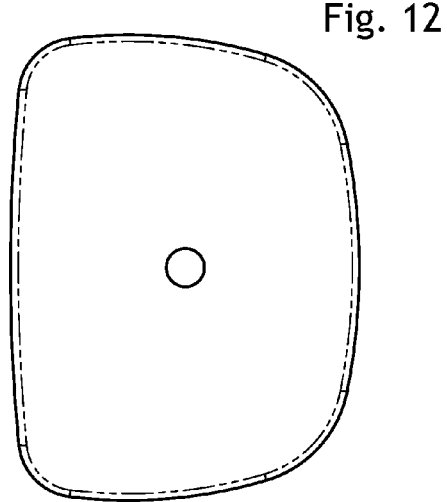
FIGS. 12 & 13 are top and side views of a representative irregular polygon shaped implant illustrating variable lordosis (or kyphosis) of arcuate surfaces that are inclined relative to each other about a central Transverse plane, and represented by variable heights measured from the anterior and posterior sides of the implant.

In any one of the embodiments described herein, at least one protrusion is configured to puncture the adjacent endplate when the implant is positioned between vertebrae. In some embodiments, the heights of the various protrusions may not all be the same. For example, as shown in FIGS. 37 & 39, the truncated cone 131 may be set at one height, whereas the other smaller diameter conic protrusions 133 may have a different height. As just noted, embodiment 130 features a combination of an enlarged central protrusion 131 with a blind hole 132 in addition to one or more protrusions 133 on the surface 135, comprising combined features of previous embodiments. All versions of this embodiment can be incorporated with any previously mentioned perimeter geometries (22, 31 and 41) with superior and inferior surfaces positioned either approximately parallel to each other when viewed perpendicular to the coronal plane or at a lordotic angle 47, (FIGS. 11& 12). Additionally, each variation of this embodiment can be incorporated with a roughened, coated or porous surface 122 (FIG. 36), as previously described.

Alternate configurations of this implant include embodiments comprising irregular polygon shapes, or irregular Reuleaux polygons. One such embodiment 140 is now illustrated in (FIGS. 40-43) comprises a fin or keel shaped abutment 142 on the surface 141 that could be either the inferior surface or the superior surface. This abutment is intended to prevent articulation of surface 141 against the adjacent vertebral body endplate (either 20 or 21 in FIG. 3) while allowing the opposite surface 143 to freely articulate against its adjacent vertebral body endplate. As with previously mentioned protrusions, the height 144 of the fin abutment 142 will be sufficient to penetrate the cartilage endplate (either 20 or 21) and into the vertebral body (either 18 or 19 respectively), while not being tall enough to create difficulty during implantation. This height can range between 0.3-2.5 mm, and ideally ranges between 0.6-1.5 mm. The length 145 of the abutment 142 can range anywhere between 20%-80% of the implant anterior to posterior (A/P) dimension 146. The fin sectional geometry 147 is generally rectangular with beveled surfaces 151 at the apex 148 or any geometry where the base 149 is larger than the apex 148. The non-articulating surface 141 can either be relatively smooth, or comprise a textured, roughened, porous coated, or a sintered porous surface 152 (FIG. 44) to further ensure that the surface does not articulate relative to the adjacent vertebral endplate when implanted.

In some embodiments, at least one of the first bearing surface and the second bearing surface comprises at least one fenestration. As used herein, a fenestration is any hole, window or opening, of any size or shape, in the surface of the implant. The at least one fenestration may be circular or non-circular in profile, and/or a blind void or hole 162, 181. The fenestration may also be a ridge and groove combination 171-174 in a surface. Or more than one fenestration may be present, with each having a different configuration 181, 182, 184. Examples of various non-limiting configurations of fenestrations are illustrated in FIGS. 45-47.

Embodiment 160 (FIG. 45) employs two or more cavities 162, in addition to a keel, on surface 161 in order to promote bony ingrowth, further immobilizing the implant relative to the adjacent vertebral body endplate when implanted. The section or perimeter of each cavity can either be circular, as preferred for manufacturing reasons, or be any polygon or closed curve geometry The diameter or equivalent diameter can range from 0.5 mm to 3.0 mm. The depth of the cavity can range between 0.5 mm to a depth that is within 1.0 mm of breaking through the opposite surface.

Yet another embodiment 170 (FIG. 46) features one or more ridges 171 protruding from surface 174 that further immobilize surface 174 from articulating against the adjacent vertebral endplate when implanted. The trajectory 173 of the ridge sectional geometry 172 can be a line or any curve whose path is not parallel to the length 145 of the fin abutment 142. A first preferred orientation is perpendicular to the fin. A second preferred orientation is between 15°-45° offset from perpendicular, pointing toward the anterior of the device. In this orientation, insertion into the joint space is enhanced, while removal or unintentional anterior movement is hindered. The section 172 of the ridge(s) can be triangular or any geometry where the base of the section merging with surface 174 is greater than the apex or tip of the ridge. The height of the ridge section projected from the surface 174 can range from 0.3 mm to 0.8 mm. The width of the base of the ridge(s) can range between 0.5 mm to 1.5 mm. Yet another version of this embodiment 180 (FIG. 47) combines the cavities 181 and ridges 182. Versions 160, 170 and 180 of this embodiment can either have relatively smooth surfaces or textured surfaces as defined by 152. All versions of fins, fenestrations and ridges illustrated in these embodiments can be incorporated with any of the previously mentioned perimeter geometries (22, 31 and 41) with superior and inferior surfaces positioned either approximately parallel to each other when viewed perpendicular to the coronal plane or at a lordotic angle 47, (FIG. 12).

In any one of the embodiments herein, at least one of the first bearing surface and the second bearing surface is polished, wherein the at least one polished bearing surface has a surface finish ≤4 RMS. In a preferred embodiment, the at least one of the first bearing surface and the second bearing surface is an articulating surface.

In some embodiments, exactly one of the surfaces is an articulating surface and at least a portion of the other of the surfaces is a textured surface. In some embodiments, at least a portion of at least one of the first surface and the second surface is textured.

Still further, in other embodiments, at least a portion of both of the first surface and the second surface is textured, as illustrated in non-limiting FIGS. 36, 44, 60, 61, and surfaces 122, 152. In some preferred embodiments, such as FIGS. 60, 61 both of the first surface and the second surface is a non-articulating surface, wherein at least a portion of both of the first surface and the second surface is a fusion surface. In such a preferred embodiment, at least a portion of the first surface or the second surface comprises a surface finish ≥125 RMS. Typically, these surfaces are textured and/or porous to some degree.

In any one of the embodiments described herein, one or more of the bearing surfaces comprise a textured surface, wherein the textured surface is a roughened surface configured to receive a fixation compound. Such surfaces may be machined textured, laser finished textured surfaces, chemically treated (i.e.: acid etched), or comprise a metallurgically applied coating. In some embodiments of the implants, one or more bearing surfaces may comprise a textured surface, wherein the textured surface is a porous coating. In some embodiments, the porous coating is intended to replicate the pore structure of cancellous bone. Typical materials for textured and porous coated surfaces include: CPTi, CoCr beads, tantalum, porous PEEK, etc. In general, a coating can be configured from any chemically compatible material that will securely bond to the base material of the implant. Alternatively, a non-articulating surface may comprise one or more fenestrations, wherein a fenestrated surface is a surface configured to receive a fixation compound.

As defined herein, a fixation compound may comprise a biologic or polymerizing cements. Biologic examples include morselized bone graph or paste, or any comparable bone-graft-substitute material, cells, proteins, biologic glue, tissue sealants and fibrin sealants. Examples of polymerizing cement include polymethyl methacrylate (PMMA or Plexiglas), glue, cement, epoxy, bonding agent, fixative, paste, adhesive, adherent, binding agent, sealant, mortar, grout or any compatible synthetic, self-curing organic or inorganic material used to fill up a cavity or to create a mechanical fixation. Alternatively, the fixation compound may comprise a combination of any one of the aforementioned biologic and polymerizing cements. Fixation compounds may be used to permanently fix an implant to a surface; or alternately may be used to permanently bond assembled (implant) components together.

Provided herein is a disk-like implant adapted for placement between adjacent vertebral endplates comprising: a first endcap having a first outer surface and first inner surface and a first outer radial edge; a second endcap having second outer surface and second inner surface and a second outer radial edge, an intermediate core having an upper surface and lower surface configured to mate between the first inner surface and the second inner surface; at least one protrusion on at least one endcap surface, wherein the at least one protrusion is configured to contact a portion of at least one adjacent vertebral endplate.

Referring now to non-limiting examples illustrated in FIGS. 48-59, are numerous examples of disk-like (or alternatively, "disc-like") implants comprising a first and second endcap and an intermediate core.

In any one of the following embodiments, the first endcap surface and second endcap surface are each configured to have an external bearing geometry configured to conform to the geometry of adjacent endplate surfaces.

In any one of the embodiments, the first inner surface and second inner surface is configured to mate with the intermediate core, In some embodiments, the first outer surface is an articulating surface. In some embodiments, the second outer surface is an articulating surface.

In some embodiments, the first outer surface and second outer surface geometries are the same and comprise constant arcuate radii of curvature. In other embodiments, the first outer surface and second outer surface comprise different geometries. In still other embodiments, the first outer surface and second outer surface geometry are generally spherical.

In some embodiments, only the first outer bearing surface geometry is generally spherical. In others, only the first outer bearing surface geometry is generally spherical to flat. In some embodiments, the second outer bearing surface geometry is generally spherical. In still others, the second outer bearing surface geometry generally spherical to flat. In still others, the second outer bearing surface geometry is generally flat with spherical radiused edges blending to the sides. In any one of the embodiments described herein, the spherical geometry may vary from one anatomic plane to another plane.

Referring now to FIGS. 48-51, the articulating implant 190 comprises a shock-absorbing core 191 sandwiched between the first and second endcaps 194. This core 191 imparts a cushioning effect in place of the natural disc nucleus. The durometer of the shock-absorbing core/ring would be selected to provide anatomically appropriate stiffness to replace the natural disc stiffness, yet be selected from polymers having high compressive wear and fatigue resistance. This core 191 would be permanently bonded to the internal end cap surfaces 195 of the two end caps 194 of implant 190 eliminating the potential for any relative movement at the interface 197 between the core 191 and the end caps 194. The height or thickness 192 of the intermediate core 191 comprises a range between 1.0 mm and 15.0 mm. The height 193 of the individual endcaps 194 will comprise a range between 1.0 mm 6.0 mm. Together, the height of the insert 191 plus two end caps 194 will comprise the overall arcuate height 199 of the implant. Preferred embodiments would comprise cervical implants with an overall arcuate height 199 similar to 23 defined in FIG. 5, ranging between 4.0-12.0 mm. Similarly, preferred embodiments of lumbar implants would have an overall height ranging between 8.0-24.0 mm. Ideally, the superior and inferior bearing surfaces 196 would be highly polished, as well as one protrusion 198 centered on both surfaces 196, as previously described.

In another version of a non-limiting articulating embodiment 200 (FIGS. 52-55), the endplates incorporate a pocket 201 in the interior surface of the end caps 202 and corresponding protrusions 204 on both surfaces of the shock-absorbing core 203. The intent of the core protrusions 204 and end cap pockets 201 is to further prevent the possibility of movement of the core 203 relative to the end caps 202 in addition to permanent bonding of the interfaces between these components. The height 205 of both end cap pockets 201 will range from 0.5 mm to 1.5 mm. The diametral size and height of the core protrusions 204 can range from a loose slip fit to a line-to-line interference fit (as is commonly known in the industry) with the end cap pockets 201. As previously noted, the core would be permanently bonded to the mating endcaps. Ideally, the superior and inferior bearing surfaces 206 would be highly polished, as well as one protrusion 207 centered on both surfaces 206, as previously described.

In still another non-limiting embodiment, not displayed, the previous embodiment (200) would comprise and inverse configuration, wherein there would are pockets in the core and corresponding protrusions in the end caps, in addition to permanent bonding of the interfaces.

In yet another non-limiting embodiment, illustrated by implant 210 (FIGS. 56-58) the endcaps comprise a sliding fit mechanism comprising of a protrusion 211 that engages a corresponding hole 212 in hub 218, with a sliding fit. The purpose of this sliding fit mechanism is to minimize shear stress on the polymer or hydrogel core 213 and improve fatigue life of this core component. The shock-absorbing core 213 has a corresponding thru-hole 214 that will provide clearance with the hub 218 sliding fit mechanism. This core 214 would be permanently bonded to the end caps 215 at the interfaces 220 created by the interior surfaces of the endcaps 219 and the superior and inferior surfaces 217 of the shock-absorbing core 213. All versions of this embodiment can be incorporated with any of the previously mentioned perimeter geometries (22, 31 and 41) with superior and inferior surfaces positioned either approximately parallel to each other (as illustrated in FIG. 11) when viewed perpendicular to the coronal plane, or at a lordotic angle 47, (as illustrated in FIG. 12). Ideally, the superior and inferior bearing surfaces 216 would be highly polished, as well as one protrusion 221 centered on both surfaces 216, as previously described.

In some variations of embodiment 210 (FIGS. 56-58), the first protruding attachment means is a protruding cylinder with a hole, centered about the central axis. In some embodiments, the first protruding attachment means is a protruding polygon having three or more sides with a hole, centered about the central axis. In some embodiments, the hole is a polygon having three or sides. Still further, in some embodiments, the hole may be a blind hole or a tapered hole. In some embodiments, the tapered hole comprises a Morse taper.

In corresponding variations of embodiment 210, the second protruding attachment means is a protruding cylinder with a hole, centered about the central axis. In some embodiments, the second protruding attachment means is a protruding polygon with a hole, centered about the central axis. In some embodiments, the hole is polygonal. Still further, in some embodiments, the hole may be a blind hole or a tapered hole. In some embodiments, the tapered hole comprises a Morse taper.

Figure 63:
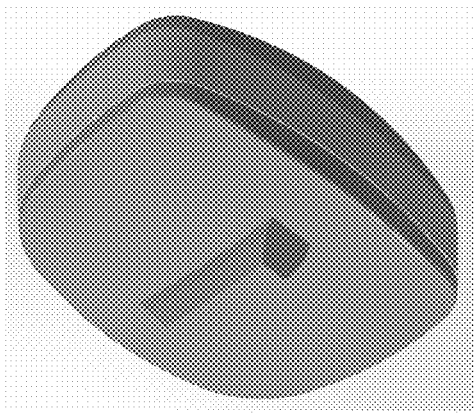
FIG. 63 is a representative isometric view of a Reuleaux-shaped, assembled unitary implant comprising an intermediate shock-absorbing core permanently bonded between the upper and lower endcap components.
Figure 64:
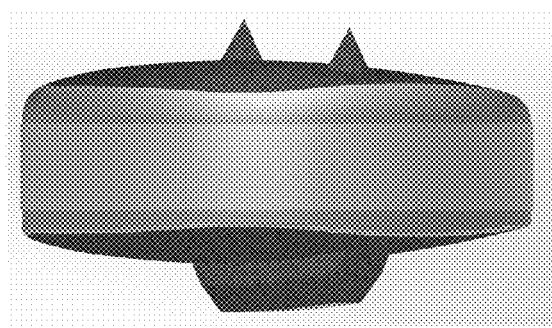
FIGS. 64 and 65 are representative ISO views of additional salvage/fusion devices, comprising textured or bone-ingrowth promoting and/or articulating surfaces on the bearing endplate surfaces.
Figure 65:
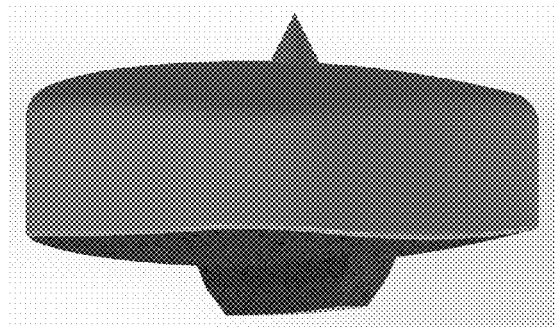

It is further understood that although the non-limiting examples of the implants illustrated herein for these configurations (FIGS. 48-59) are circular in plan-view, an equally preferred or ideal planar geometry of these implants is elliptical or an irregular Reuleaux polygon, such as illustrated in FIG. 63.

In any of the aforementioned embodiments, the first inner surface and the second inner surface are textured surfaces, wherein the textured surface is surface configured to receive a fixation compound intended to bond an intermediate core to the implant.

In any one of the embodiments, the intermediate core is configured to be shock-absorbing and biocompatible. In some embodiments, the intermediate core is a hydrogel. In some embodiments, the intermediate core is a polymer.

In any one of the embodiments, the intermediate core upper surface is bonded to the first inner surface and the intermediate core lower surface is bonded the second inner surface, and the bond is permanent.

In any one of the embodiments, the first inner surface and the second inner surface are essentially parallel to each other about a central transverse plane.

In some embodiments, the first inner surface and the second inner surface are not parallel, and are inclined toward each other about a central transverse plane, (not shown). More specifically, implants 190, 200 (FIGS. 48-55), may be configured to have an intermediate core, with inclined superior and inferior surfaces intended to replicate specific lordotic or kyphotic spinal angles.

Ideally, any of the circular embodiments described throughout this specification comprise diametral dimensions in the range of 17.0 mm-45.0 mm, (corresponding to the anticipated A/P dimension [sagittal plane depth] of the vertebral endplate), whereas the height of the spherical radius of curvature for the endcap bearing surface comprises a range between 0.1 mm (generally flat) and 5.0 mm.

Alternatively, in other preferred embodiments described throughout this specification comprising elliptical or irregular Reuleaux polygon configurations, the implants comprise corresponding M/L dimensions (coronal plane, width) in the range of 24.0 mm-69.0 mm, in addition to the A/P (sagittal plane, depth) and height of the spherical radius of curvature dimensions described previously.

Additionally, in some embodiments the first outer surface and second outer surface are inclined to each other about a central transverse plane. The angle of inclination, as measured in the sagittal plane, is representative of the desired degree of lordosis (or kyphosis) to be incorporated into the implant. Ideally, any of the circular, elliptical or irregular Reuleaux polygon-shaped implants described throughout this specification comprise a lordosis included angle between the ranges of 0°-20°.

In some embodiments, the inclined angle, or lordosis (or kyphosis) angle is incorporated into the intermediate core, i.e.: FIGS. 48-55. In other embodiments, the inclined angle, or lordosis (or kyphosis) angle is incorporated into the endcaps, i.e.: FIGS. 56-59.

In still other embodiments, the arcuate radii of curvature of the first and second outer surfaces are essentially mirror imaged about a central transverse plane.

In some embodiments, the implant comprises an anterior-posterior dimension that is greater than the overall arcuate height of the implant. In some embodiments, the ratio of the anterior-posterior dimension to the overall arcuate height is at least 1.01:1. In some embodiments, the ratio of the anterior-posterior dimension to the overall arcuate height is at least 1.1:1. In still other embodiments, the ratio of the anterior-posterior dimension to the overall arcuate height is at least 1.2:1. In still other embodiments, the ratio of the anterior-posterior dimension to the overall arcuate height is at least 1.5:1, or at least 2.0:1.

In some embodiments, the implant comprises a medial-lateral dimension that is greater than the overall arcuate height of the implant. In some embodiments, the ratio of the medial-lateral dimension to the overall arcuate height is at least 1.01:1. In other embodiments, the ratio of the medial-lateral dimension to the overall arcuate height is at least 1.1:1. In still other embodiments, the ratio of the medial-lateral dimension to the overall arcuate height is at least 1.2:1. In still other embodiments, the ratio of the medial-lateral dimension to the overall arcuate height is at least 1.5:1; at least 2.0:1, at least 3.0:1, or at least 4.0:1.

In some embodiments, at least one of the first outer surface and the second outer surface is a bearing surface. Still further, in some embodiments, at least one of the first outer surface and the second outer surface is a polished bearing surface, wherein the at least one polished bearing surface has a surface finish ≤4 RMS. Further still, at least one of the first outer surface and the second outer surface is an articulating surface.

In some embodiments, exactly one of the bearing surfaces is an articulating surface and at least a portion of the other of the surfaces is a textured surface. In some embodiments, at least a portion of at least one of the first outer surface and the second outer surface is textured. In still other embodiments, at least a portion of both of the first outer surface and the second outer surface is textured. Still further, in some embodiments, both the first outer surface and the second outer surface is a non-articulating surface. In some of the preceding embodiments, the textured surface comprises more than one protrusion configured to contact a portion of at least one adjacent vertebral endplate.

In other embodiments, at least a portion of both of the first outer surface and the second outer surface is a fusion surface. In some embodiments, the fusion surface comprises more than one protrusion configured to penetrate a portion the adjacent vertebral endplate.

In some of the preceding embodiments, at least a portion of the first outer surface or the second outer surface comprises a surface finish ≥125 RMS. In some embodiments, a surface comprising a surface finish ≥125 RMS is a textured or porous coated surface or a surface intended to mimic a cancellous bone structure. In some embodiments, a textured or porous coated surface is a surface configured to receive a fixation compound.

Referring now to two non-limiting examples shown in FIGS. 60-62, 64, 65, are fusion or salvage implant embodiments. Salvage implants refer to those instances where a former implant (of any type) has failed or requires replacement. Fusion or salvage implants may incorporate various forms of traditional fusion augmentation hardware such as screws and plates and may also include other supplemental augmentation such as stabilizing structures attached to the adjacent vertebrae to further capture the implant within the vertebral joint. These supplemental augmentation stabilizing structures may include allograft, autograft, synthetic graft materials, or combinations thereof. Additionally these supplemental augmentation stabilizing structures may further be augmented with growth promoting materials such as collagen, fibrin, chondrocytes, stem cells, peptides or growth hormones or other growth promoting factors.

In any one of the preceding fusion embodiments, the implant is circular in the transverse (horizontal) plane.

In any one of the preceding embodiments, the implant is elliptical in the transverse (horizontal) plane, wherein the medial-lateral (M/L) dimension is greater than the anterior-posterior (A/P) dimension.

In any one of the preceding embodiments, the implant is an irregular Reuleaux polygon in the transverse (horizontal) plane, wherein the major medial-lateral (M/L) dimension is greater than the major anterior-posterior (A/P) dimension.

In any one of the preceding fusion embodiments, the implant is also configured with an intermediate core (not shown), configured to be a shock absorber that would mimic the natural disc, while also replacing lost disc height.

In any one of the preceding embodiments, the implant is configured for use in the spine of a human, wherein the implant is a spinal disc implant.

In any one of the preceding embodiments, the implant is configured for use in the spine of a human, wherein the implant is a spinal fusion implant.

In any one of the preceding embodiments, the implant is configured for use in the spine of a human, wherein the implant comprises an articulating surface on one side and a fusion surface on the opposite side.

In any one of the preceding embodiments, the implant is a unitary disc implant comprising no independent moving components.

In some of the preceding embodiments, the implant is a unitary disc implant comprising no independent moving components, as assembled.

In some embodiments, the implant is a joint implant, having applications in artificial limbs, robotics, or other joints and mechanisms. In some embodiments, the implant is a medical implant having applications for veterinary applications. In still other preferred embodiments, the implant of the subject specification is a human medical implant intended for the spine.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A unitary implant adapted for placement between adjacent surfaces of a joint comprising:
    an inflexible interbody device having no moving components;
    a first generally spherical articular bearing surface centered about a central axis and generally conforming to a geometry of a first adjacent joint surface; and a second generally spherical bearing surface centered about a central axis and generally conforming to a geometry of a second adjacent joint surface;
    an outer radial edge surface;
    a first protrusion extending from the first bearing surface about the central axis of the interbody device, wherein the first protrusion is configured to contact and puncture a central portion of the first adjacent joint surface endplate when the implant is positioned between vertebrae, and
    wherein the first protrusion and generally spherical articular bearing surface is adapted to allow rotation and restore near-normal motion between the interbody device and the first adjacent surface.

2. The unitary implant of claim 1, further comprising:
    a second protrusion extending from the second bearing surface about the central axis of the interbody device, and
    the second bearing surface is a second articular bearing surface,
    wherein the second protrusion is configured to contact and puncture a central portion of the second adjacent surface endplate when the implant is positioned between vertebrae, and
    wherein the second protrusion and second articular bearing surface is adapted to allow rotation and restore near-normal motion between the interbody device and the second adjacent surface.

3. The implant of claim 2, wherein the second protrusion is conical.

4. The implant of claim 2, wherein the first protrusion or second protrusion comprises:
    a spike,
    a curved cone,
    a truncated cone, or
    a cylinder.

5. The implant of claim 2, wherein the curvature of the first bearing surface and the second bearing surface are centered about a central axis and generally flat near the central axis and transition to spherical curvature about the outer radial edge surface.

6. The implant of claim 1, wherein the first protrusion is conical.

7. The implant of claim 1, further comprising:
    at least a second and third protrusion, on the second bearing surface adapted to prevent movement between the second bearing surface and the second adjacent surface,
    a textured surface finish configured to promote fixation of the second bearing surface to the second adjacent surface;
    wherein the at least second and third protrusions are configured to puncture the adjacent endplate when the implant is positioned between vertebrae to resist rotation or migration of the interbody device while still allowing for rotation between the between the interbody device and the first adjacent surface.

8. The implant of claim 7, further comprising a non-articulating surface texture finish on the second bearing surface, wherein the surface texture comprises;
    a grit blasted texture,
    a porous texture,
    a laser sintered texture,
    an etched surface,
    a roughened porous spray titanium,
    a hydroxyapatite coating,
    a porous coating, or
    a porous formation, and
    configured to promote fibrous tissue on-growth, fibrous tissue ingrowth, bone on-growth or bone ingrowth.

9. The implant of claim 1, further comprising a generally circular shape about a central axis.

10. The implant of claim 1, further comprising a non-circular shape about a central axis.

11. The implant of claim 10, further comprising a keel shaped protrusion extending from the second bearing surface configured to penetrate the endplate of the second adjacent surface to prevent rotation or migration between the second adjacent surface and the interbody device;
    wherein the first highly polished articular surface and first protrusion promote rotation between the between the interbody device and the first adjacent surface.

12. The implant of claim 11, further comprising the second bearing surface textured finish configured with a non-articulating surface texture comprising:
    a grit blasted texture;
    a porous textures;
    a laser sintered textures;
    an etched surface;
    a roughened porous spray titanium;
    a hydroxyapatite coating;
    a porous coating; or
    a porous formation; and
    configured to promote fibrous tissue on-growth, fibrous tissue ingrowth, bone on-growth or bone ingrowth.

13. The implant of claim 1, further comprising an elliptical planar shape about a central axis.

14. The interbody device of claim 1, further comprising:
    a Reuleaux polygon planar shape comprising three or more odd number of sides; or
    an irregular Reuleaux planar shape comprising three or more odd number of sides with one or more sides having straight side edges, curved side edges or combinations of straight and curved side edges.

15. The implant of claim 1, further comprising generally spherical articular curvature of the first bearing surface and the second bearing surface comprising increasing arcuate radii of curvature centered about the central axis from the outer radial edge surface to a zone near the central axis of the interbody device.

16. The implant of claim 1, wherein the curvature of the first bearing surface and the second bearing surface are different from each other.

17. The implant of claim 1, wherein the first bearing surface and the second bearing surface are inclined to each other about a central transverse plane and centered about the central axis.

18. The implant of claim 1, wherein the first bearing surface or second bearing surface comprises:
    pyrolytic carbon,
    titanium nitride,
    tantalum, cobalt,
chromium,
alumina,
zirconia,
silicon carbide,
silicon nitride,
stainless steel,
PEEK,
Delrin,
diamond, or
diamond-like material.

19. A unitary disc implant adapted for placement between adjacent vertebral surfaces of a spinal joint comprising:
   a rigid interbody device having no moving components;
   a first polished, generally spherical articular bearing surface;
   a second polished, generally spherical articular bearing surface;
   a first protrusion centered about a central axis on the first bearing surface configured to penetrate a central portion of a first adjacent vertebral surface when the implant is positioned between vertebrae; and
   a second protrusion centered about the central axis on the second bearing surface configured to penetrate a central portion of a second adjacent vertebral surface when the implant is positioned between vertebrae;
   wherein the first protrusion and second protrusion are adapted to promote rotation and restore near-normal motion between the interbody device and the first and second adjacent surfaces.

20. A unitary disc implant adapted for placement between adjacent vertebral surfaces of a spinal joint comprising:
   a rigid interbody device having no moving components;
     a first generally spherical articular bearing surface: and
     a second generally spherical bearing surface;
     a first protrusion on the first bearing surface centered about a central axis of the intervertebral body configured to penetrate a central portion of the first adjacent vertebral surface when the implant is positioned between vertebrae and adapted to promote rotation and restore near-normal motion between the interbody device and the first adjacent surface;
   at least a second protrusion on the second bearing surface configured to penetrate the endplate of the second adjacent vertebral surface when the implant is positioned between vertebrae; and
   a surface texture on the second bearing surface;
   wherein the first and second bearing surfaces are generally spherical and configured to conform to the geometry of first and second adjacent vertebral joint surfaces, and
   wherein the at least second protrusion and the surface texture on the second bearing surface are adapted to prevent movement between the second bearing surface and the second adjacent surface and configured to promote fibrous tissue on-growth, fibrous tissue ingrowth bone on-growth or bone ingrowth.

* * * * *